United States Patent
Meng et al.

(10) Patent No.: US 9,273,007 B2
(45) Date of Patent: Mar. 1, 2016

(54) PROCESSES FOR THE PREPARATION OF 1-ARYL-5-ALKYL PYRAZOLE COMPOUNDS

(71) Applicant: Merial Limited, Duluth, GA (US)

(72) Inventors: Charles Q. Meng, Grayson, GA (US); Loic Patrick Le Hir de Fallois, Atlanta, GA (US); Hyoung Ik Lee, Cary, NC (US); Xinxi Zhan, Beijing (CN); Jean Robert Labrosse, Saint Hilaire de Beauvoir (FR); Michel Mulhauser, Saint Didier au Mont d'Or (FR)

(73) Assignee: MERIAL, INC., Duluth, GA (US)

( * ) Notice: Subject to any disclaimer, the term of this patent is extended or adjusted under 35 U.S.C. 154(b) by 0 days.

(21) Appl. No.: 14/543,341

(22) Filed: Nov. 17, 2014

(65) Prior Publication Data

US 2015/0073153 A1    Mar. 12, 2015

Related U.S. Application Data

(63) Continuation of application No. 13/867,699, filed on Apr. 22, 2013, now Pat. No. 8,937,185.

(60) Provisional application No. 61/635,969, filed on Apr. 20, 2012.

(51) Int. Cl.
*C07D 231/18* (2006.01)

(52) U.S. Cl.
CPC ................................. *C07D 231/18* (2013.01)

(58) Field of Classification Search
CPC ................................................. C07D 231/18
See application file for complete search history.

(56) References Cited

U.S. PATENT DOCUMENTS

| | | | |
|---|---|---|---|
| 4,772,312 | A | 9/1988 | Gehring et al. |
| 4,810,720 | A | 3/1989 | Jensen-Korte et al. |
| 4,826,867 | A | 5/1989 | Jensen-Korte et al. |
| 4,909,832 | A | 3/1990 | Gehring et al. |
| 4,963,575 | A | 10/1990 | Buntain et al. |
| 5,232,940 | A | 8/1993 | Hatton et al. |
| 5,306,694 | A | 4/1994 | Phillips et al. |
| 5,451,598 | A | 9/1995 | Salmon |
| 5,817,688 | A | 10/1998 | Huang et al. |
| 6,069,157 | A | 5/2000 | Banks et al. |
| 7,385,063 | B2 | 6/2008 | Arrhenius et al. |
| 7,759,381 | B2 | 7/2010 | Lee et al. |
| 2005/0020564 | A1 | 1/2005 | Atkinson et al. |

FOREIGN PATENT DOCUMENTS

| | | |
|---|---|---|
| EP | 0 257 479 | 3/1988 |
| WO | WO 98/28278 | 7/1998 |
| WO | WO 2005/023775 | 3/2005 |
| WO | WO 2006/000311 | 1/2006 |

OTHER PUBLICATIONS

"New application of heterocyclic diazonium salts. Synthesis of pyrazolo [3,4-d] [1,2,3]triazin-4-ones and imidazo[4,5-d][1,2,3]triazin-4-ones", Colomber and Moyano, *Tetrahedron Letters* 52 (2011), 1561-1565.
"Synthesis of 5-chloropyrazoles by Chlorodediazoniation with Sulfur Dioxide," Yamamoto et al., *J. Heterocyclic Chem.*, 28, (1991), 1545.
"Pd/C-mediated synthesis of a-pyrone fused with a five-membered nitrogen heteroaryl ring: A new route to pyrano[4,3-c]pyrazol-4(1H)-ones", Gorja et al., *Beilstein Journal of Organic Chemistry*, 2009, 5(64).
"The diazotization of Heterocyclic Primary Amines," R.N. Butler, *Chem. Rev.*, 1975, 75(2), 241-257.
"4-Arylation of 3-alkoxypyrazoles", Guillou et al, *Tetrahedron*, 2009, 65(17), 3529-3535.
"Synthesis, Characterization and Bioactivity of Fipronil Derivatives as a Lead for a New Insecticide", Xiaohua et al., *Indian Journal of Chemical Technology*, May 2010, 17, 215-219.
"Palladium-catalyzed Cross-coupling Reactions of Organoboron Compounds", A. Miyaura and Suzuki, *Chem. Rev.*, 1995, 95, 2457.

*Primary Examiner* — Samantha Shterengarts
(74) *Attorney, Agent, or Firm* — Judy Jarecki-Black; Peter Dolan Merial, Inc.

(57) ABSTRACT

Provided are improved processes for the preparation of 1-aryl pyrazole compounds of formula (I) and (IB):

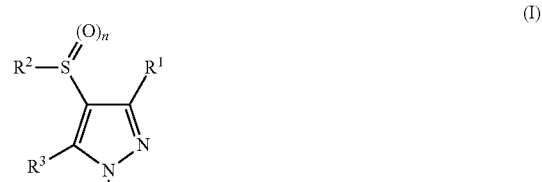

(I)

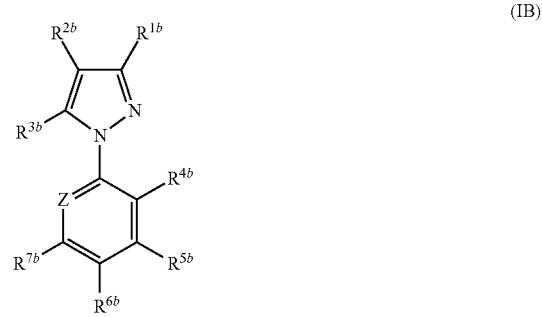

(IB)

which are substituted at the 5-position of the pyrazole ring with a carbon-linked functional group. The process described are efficient and scalable and do not utilize hazardous sulfenyl halide reagents.

20 Claims, No Drawings

PROCESSES FOR THE PREPARATION OF 1-ARYL-5-ALKYL PYRAZOLE COMPOUNDS

INCORPORATION BY REFERENCE

This application is a continuation of, and claims benefit of, co-pending U.S. patent application Ser. No. 13/867,699, which claims benefit of the US Provisional patent application no. 61/635,969, filed on Apr. 20, 2012, which is incorporated herein by reference in its entirely.

FIELD OF THE INVENTION

The present invention relates to processes for the preparation of 1-aryl pyrazole compounds, of general formulae (I) and (IB):

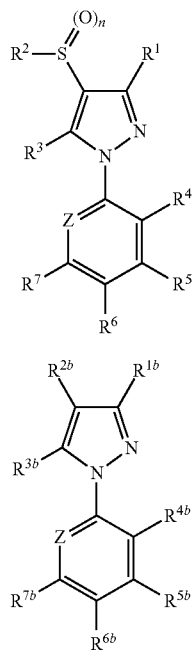

wherein:
$R^1$, $R^2$, $R^3$, $R^4$, $R^5$, $R^6$, $R^7$, Z, $R^{1B}$, $R^{2B}$, $R^{3B}$, $R^{4B}$, $R^{5B}$, $R_{6B}$, $R^{7B}$ and W and n are as defined below. The compounds of formula (I) and (IB) are useful to treat and protect animals against ectoparasites.

BACKGROUND OF THE INVENTION

Animals such as mammals and birds are often susceptible to parasite infestations. These parasites may be ectoparasites, such as fleas (Ctenocephalides felis, Ctenocephalides sp. and the like), ticks (including Rhipicephalus sp., Ixodes sp., Dermacentor sp., Amblyomma sp. and the like), mites (Demodex sp., Sarcoptes sp., Otodectes sp. and the like), lice (Trichodectes sp., Cheyletiella sp., Linognathus sp., and the like), and flies (including Hematobia sp., Musca sp., Stomoxys sp., Dermatobia sp., Cochliomyia sp.), mosquitoes (family Culicidae) and the like. Animals may also be susceptible to infection by endoparasites such as filaria and worms.

Compounds that exhibit a high degree of activity against a wide range of ectoparasites including arthropods and insects are known in the art. One such class of compounds is the arylpyrazoles which are referred to, for example, in U.S. Pat. Nos. 5,122,530; 5,246,255; 5,576,429; 5,885,607; 6,010,710; 6,083,519; 6,096,329; 6,685,954; EP 0 234 119 and EP 0 295 117 (U.S. Pat. Nos. 5,232,940; 5,547,974; 5,608,077; 5,714, 191; 5,916,618 and 6,372,774); EP 0 352 944 (U.S. Pat. No. 4,963,575); EP 0 780 378 (U.S. Pat. Nos. 5,817,688; 5,922, 885; 5,994,386; 6,124,339; 6,180,798 and 6,395,906); EP 0 846 686 (U.S. Pat. No. 6,069,157); and WO 98/28278, all incorporated herein by reference.

The arylpyrazoles are known to possess excellent activity against ectoparasites, such as fleas and ticks. Within this family of compounds, fipronil, 5-Amino-3-cyano-I-(2,6-dichloro-4-trifluoro-methylphenyl)-4-trifluoromethylsulfinylpyrazole, has been found to be exceptionally potent against insects and acarids. Fipronil is the active ingredient in the well-known Frontline® family of products for treatment and control of fleas, ticks and chewing lice in cats and dogs. Fipronil binds to the gamma aminobutyric acid (GABA) receptors in the cell membranes of invertebrate neurons, functionally stabilizing the closed form of the channel resulting in death. Fipronil has the following chemical structure:

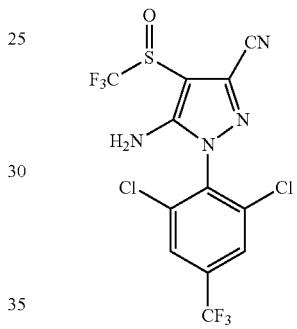

Fipronil has been commercialized for several years with use in both the agricultural sector and for the protection of animals against ectoparasites. Accordingly, efficient processes to prepare fipronil on a large scale are known.

Recently, 1-aryl-5-alkyl pyrazole derivatives that exhibit exceptional activity against ectoparasites, including fleas and ticks, were reported in WO 2008/005489 and US 2008/ 0031902 (now U.S. Pat. No. 7,759,381 B2) to Lee et al., incorporated herein by reference. The 1-aryl-5-alkyl pyrazole compounds differ from fipronil, inter alia, in that they are substituted at the 5-position of the pyrazole ring with an alkyl or haloalkyl group rather than an amino group. In addition, certain 1-aryl-5-alkylpyrazole compounds described in the publications include mixed halogen substitution on the phenyl ring and on the 4-sulfinyl group. The known processes for the preparation of fipronil are not appropriate for the synthesis of the new 1-aryl-5-alkylpyrazole compounds.

WO 02/058690 and US 2004/0087627 refer to the synthesis of pyrazoles bearing a (2,2,2-trifluoro-1-hydroxy-1-(trifluoromethyl))ethyl substituent by reaction of a 1,3-diketone and phenylhydrazine bearing the 1-hydroxy-1-(trifluoromethyl)ethyl substituent (Scheme 4, page 11, US 2004/ 0087627). The synthesis of a specific compound by this method, 5-methyl-1-[(1-hydroxy-1-(trifluoromethyl)ethyl) phenyl)-1H-pyrazole-3-carboxylic acid ethyl ester is mentioned (US 2004/0087627, pages 23-24, Example 8). However, there appeared to be no examples where a 3,4,5-disubstituted pyrazole is prepared except in the presence of a 5-amino group or when all three substitutions are the same (methyl).

Synthesis of 3-ester-4-unsubstituted pyrazoles is also referred to in US 2005/0020564 (page 10, Scheme 3).

WO 2008/005489 and US 2008/0031902 A1 describe the synthesis of 1-aryl-5-alkylpyrazole compounds by a process wherein 2-thio-1,3-diketone derivatives are made by reacting a sulfenyl halide reagent with 1,3-diketone compounds, which are further reacted with a suitably substituted arylhydrazine compound to produce a 1-aryl-5-alkylpyrazole compound, which may be further elaborated to produce the desired pyrazole compounds. However, the process described utilizes haloalkyl sulfenyl halide reagents (e.g. trifluoromethyl sulfenyl chloride and dichlorofluoromethyl sulfenyl chloride), which are particularly hazardous and difficult to source. Accordingly, there is a need for improved processes for the preparation of 1-aryl pyrazole compounds which contain a carbon-linked group at the 5-position of the pyrazole ring, including 1-aryl-5-alkylpyrazole compounds, that are cost effective and adaptable to scale up.

Any and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. The citation or identification of any document in this application is not an admission that such document is available as prior art to the present invention.

OBJECTS AND SUMMARY OF THE INVENTION

The invention provides improved processes for the preparation of 1-arylpyrazole compounds of formulae (I) and (IB) shown below wherein variables $R^1$, $R^2$, $R^3$, $R^4$, $R^5$, $R^6$, $R^7$, Z, $R^{1B}$, $R^{2B}$, $R^{3B}$, $R^{4B}$, $R^{5B}$, $R^{6B}$, $R^{7B}$ and W and n are defined herein.

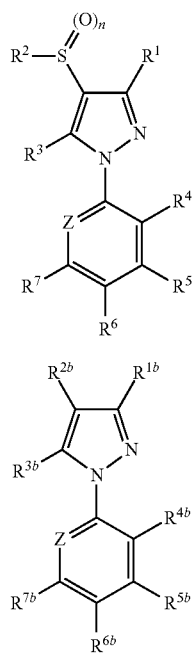

In a first aspect of the invention, a process for the preparation of the compound of formula (I) is provided which comprises (i) reacting a disulfide compound of formula (II) with an arylhydrazine of formula (III)

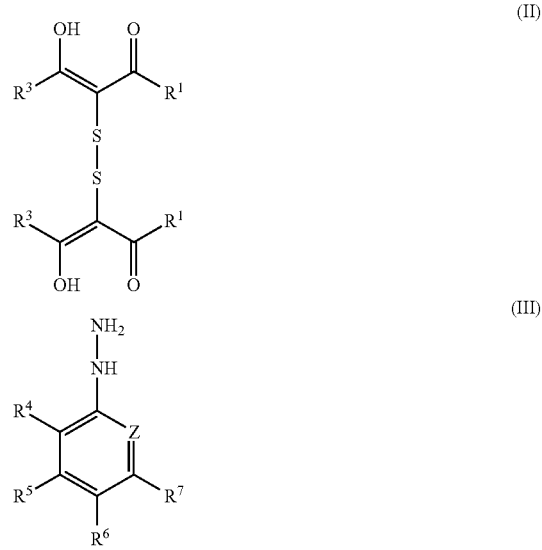

wherein $R^1$ and $R^3$ are each independently hydrogen, hydroxyalkyl, alkoxyalkyl, aminoalkyl, alkylaminoalkyl, dialkylaminoalkyl, alkyl, haloalkyl, cycloalkyl, halocycloalkyl, alkenyl, alkynyl, formyl, aryl, heterocyclyl, heteroaryl, —C(O)$R^8$, —C(O)O$R^8$, —C(O)N$R^9R^{10}$ or —C(S)NH$_2$, wherein each alkyl, cycloalkyl, alkenyl, alkynyl, aryl, heterocyclyl or heteroaryl group may optionally be substituted by one or more of halogen, hydroxy, alkoxy, alkoxyalkoxy, amino, alkylamino, dialkylamino, alkyl or haloalkylthio; alkyl or haloalkyl sulfinyl; alkyl or haloalkyl sulfonyl; nitro, cyano and —C(S)NH$_2$; and $R^4$, $R^5$, $R^6$, $R^7$ and Z are as defined for the compound of formula (I) below, to form a pyrazole disulfide of formula (IV)

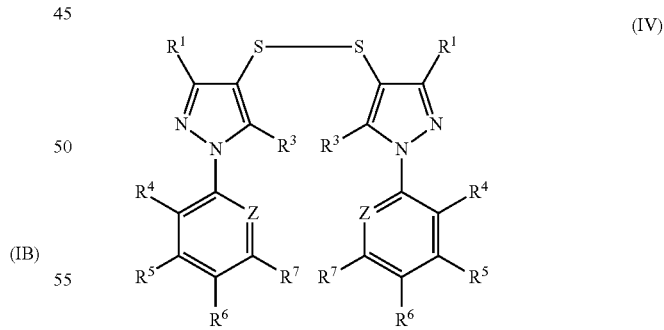

wherein $R^1$, $R^3$ $R^4$, $R^5$, $R^6$, $R^7$ and Z are as defined for the compound of formula (I); (ii) reacting the compound of formula (IV) with a compound of formula (V)

wherein $R^2$ is as defined above for the compound of formula (I) and LG is a leaving group to form a compound of formula (VI):

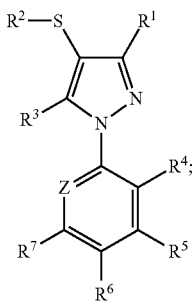 (VI)

(iii) wherein in the compound of formula (VI), if $R^1$ or $R^3$ are —C(O)OR$^8$ or —C(O)NR$^9$R$^{10}$, optionally converting the —C(O)OR$^8$ or —C(O)NR$^9$R$^{10}$ groups to cyano, hydroxyalkyl, aminoalkyl, dialkylaminoalkyl, formyl, —C(O)R$^8$ or —C(S)NH$_2$; and (iv) optionally oxidizing the —SR$^2$ group to form the compound of formula (I); wherein the sequence of steps iii) and iv) may be interchanged.

In one embodiment of the process, the disulfide of formula (II) is formed by reaction of the β-diketone of formula (VII)

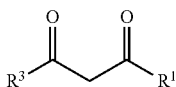 (VII)

with a disulfide dihalide reagent.

In another embodiment, in step ii) the reaction of the compound of formula (IV) with the compound of formula (V) is carried out in the presence of a reducing agent. In one embodiment, the reducing reagent is tetrakis(dimethylamino)ethylene, sodium borohydride, sodium dithionite, sodium hydroxymethanesulfinate, zinc hydroxymethanesulfinate, formic acid or sodium formate.

In another embodiment of the process, a compound of formula (I) is prepared wherein $R^2$ is alkyl or haloalkyl; $R^1$ is —C(O)OR$^8$ or —C(O)NR$^9$R$^{10}$; and $R^3$ is alkyl.

In yet another embodiment of the process, in step ii) the leaving group LG of the compound of formula (V) is iodide.

In a second aspect of the invention, a process for the preparation of the compound of formula (IB) is provided, which comprises:

(i) reacting a compound of formula (IIB):

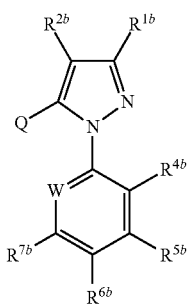 (IIB)

wherein $R^{1b}$, $R^{2b}$, $R^{4b}$, $R^{5b}$, $R^{6b}$, $R^{7b}$ and W are as defined below for the compound of formula (IB) and Q is iodo, bromo, chloro or a haloalkylsulfonate group;

with a compound of formula (IIc) or (IId):

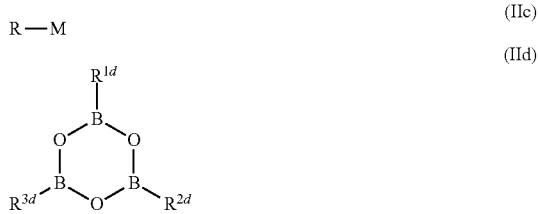

wherein R, $R^{1d}$, $R^{2d}$ and $R^{3d}$ are independently alkyl, haloalkyl, cycloalkyl, halocycloalkyl, alkenyl, alkynyl, aryl, heteroaryl or heterocyclyl, wherein each alkyl, cycloalkyl, alkenyl, alkynyl, aryl, heteroaryl or heterocyclyl group may optionally be substituted with one or more halogen, hydroxy, alkoxy, alkoxyalkoxy, amino, alkylamino, dialkylamino, nitro, cyano and —C(S)NH$_2$ groups; M is MgX, ZnX, RZn, BY$_2$, BF$_3$ or SnR'$_3$; X is iodo, bromo or chloro; Y is OH or alkoxy, or each Y may be an alkoxy group which is part of a glycol derivative Y—(CR"R"')$_a$—Y where R" and R"' are independently hydrogen and C$_1$-C$_3$alkyl and a is 2, 3 or 4; and R' is alkyl or haloalkyl;

or reacting the compound of formula (IIB) with R$^{8b}$NH$_2$, (R$^{8b}$)$_2$NH, R$^{8b}$OH, R$^{8b}$SH or an enolate anion R$^{8b}$C(O)CH$_2^-$, wherein R$^{8b}$ is as defined below for the compound of formula (IB);

in the presence of a transition metal catalyst to form the compound of formula (IB);

(ii) wherein if $R^{1b}$ in the compound of formula (IB) is —C(O)OR$^{8b}$ or —C(O)NR$^{9b}$R$^{10b}$ optionally converting the —C(O)OR$^{8b}$ or —C(O)NR$^{9b}$R$^{10b}$ groups to cyano, hydroxyalkyl, aminoalkyl, dialkylaminoalkyl, formyl, —C(O)R$^{8b}$ or —C(S)NH$_2$ via functional group conversion, wherein $R^{8b}$, $R^{9b}$ and $R^{10b}$ are as defined below for the compound of formula (IB); and (iii) wherein if $R^{2b}$ is —S(O)$_m$R$^{11b}$, optionally oxidizing the group —S(O)$_m$R$^{11b}$ where $R^{11b}$ is as defined below for the compound of formula (IB) and m is 0 or 1, to form the compound of formula (IB); wherein the sequence of steps ii) and iii) may be interchanged.

In one embodiment, the compound of formula (IIB) wherein Q is I, Br or Cl is prepared by reacting a compound of formula (IIIB):

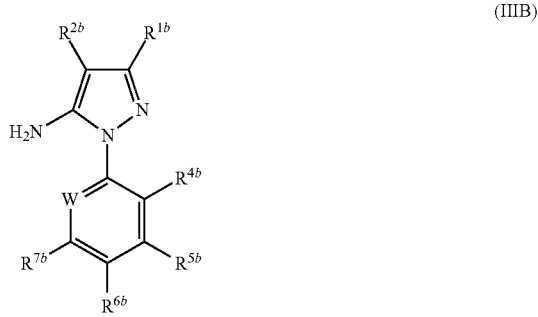 (IIIB)

wherein $R^{1b}$, $R^{2b}$, $R^{4b}$, $R^{5b}$, $R^{6b}$, $R^{7b}$ and W are as defined below for the compound of formula (IB), with a source of Br, Cl or I in the presence of a nitrite compound T-ONO where T is hydrogen or alkyl, or a salt thereof.

In another embodiment, the transition metal catalyst of step (i) is a palladium catalyst.

In another embodiment of the process, the compound of formula T-ONO is sodium nitrite, isopentyl nitrite, or tert-Butyl nitrite.

In yet another embodiment, variable Q in the compound of formula (IIB) is bromo.

In another embodiment of step (i) of the process, M in the compound of formula (IIc) is ZnX or RZn. In another embodiment, M is $BY_2$. In still another embodiment, B is $BY_2$ wherein Y is hydroxy. In another embodiment of the process, in step (i) the compound of formula (IIB) is reacted with the compound of formula (IId). In still another embodiment, the compound of formula (IIB) is reacted with is trimethylboroxine.

In another embodiment of the process, in step (i) the compound of (IIB) is reacted with a compound of (IIc) wherein M is $BY_2$ or a compound of formula (IId), wherein a base is further added to the reaction mixture. In one embodiment, the base is an alkali metal hydroxide or an alkali metal carbonate.

In one embodiment of the process, the palladium catalyst in step (i) is selected from $(Ph_3P)_4Pd$, $(Ph_3P)_2PdCl_2$, $(CH_3CN)_2PdCl_2$, $Pd_2(dba)_3$ or $(dppf)PdCl_2$.

In another embodiment, in step (i), the compound of formula (IIIB) is reacted with a compound of formula (IId) in the presence of $Pd_2(dba)_3$ and potassium carbonate.

In yet another embodiment of the process, the compound of formula (IIB) is fipronil and the compound of formula (IId) is trimethylboroxine.

In still another embodiment of the process, in the formation of the compound of formula (IIB) from the compound of formula (IIIB), T-ONO is sodium nitrite and the source of Br is HBr.

The improved processes provide for, inter alia, access to 1-aryl-5-alkyl-4-haloalkylsulfinyl or 1-aryl-5-haloalkyl-4-haloalkylsulfinyl pyrazole compounds without the use of haloalkylsulfenyl chloride reagents, which are known to be particularly hazardous and are very difficult to source. In addition, the improved processes are adaptable to scale up and provide optimum yields and quality of the desired 1-arylpyrazole compounds.

It is noted that in this disclosure and in the claims, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

It is further noted that the invention does not intend to encompass within the scope of the invention any previously disclosed compound, product, process of making the product or method of using the product, which meets the written description and enablement requirements of the U.S. Patent and Trademark Office (35 U.S.C. 112, first paragraph) or the European Patent Office (Article 83 of the EPC), such that applicant(s) reserve the right and hereby disclose a disclaimer of any previously described product, method of making the product or process of using the product. It is therefore an intention of the invention to not explicitly cover compounds, products, processes of making products or compounds, or methods of using products or compounds that are explicitly disclosed in the prior art or whose novelty is destroyed by prior art, including without limitation any prior art herein mentioned, including without limitation U.S. Pat. Nos. 5,122, 530; 5,246,255; 5,576,429; 5,885,607; 6,010,710; 6,083,519; 6,096,329; 6,685,954; EP 0 234 119 and EP 0 295 117 (eq. to U.S. Pat. Nos. 5,232,940; 5,547,974; 5,608,077; 5,714,191; 5,916,618 and 6,372,774); EP 0 352 944 (eq. to U.S. Pat. No. 4,963,575); EP 0 780 378 (eq. to U.S. Pat. Nos. 5,817,688; 5,922,885; 5,994,386; 6,124,339; 6,180,798 and 6,395,906); EP 0 846 686 (eq. to U.S. Pat. No. 6,069,157); and WO 98/28278 (all incorporated herein by reference); and, applicant(s) explicitly reserve the right to introduce into any claim a disclaimer as to any previously disclosed compound, product, process of making the product or method of using the product.

These and other embodiments are disclosed or are apparent from and encompassed by, the following Detailed Description.

DETAILED DESCRIPTION

Definitions

For the purposes of this application, unless otherwise stated in the specification, the following terms have the terminology cited below:

(1) Alkyl refers to both straight, branched carbon chains and cyclic hydrocarbon groups. In one embodiment of alkyl, the number of carbons atoms is 1-20, in other embodiments of alkyl, the number of carbon atoms is 1-12, 1-10 or 1-8 carbon atoms. In yet another embodiment of alkyl, the number of carbon atoms is 1-6 or 1-4 carbon atoms. Other ranges of carbon numbers are also contemplated depending on the location of the alkyl moiety on the molecule;

Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups, which are encompassed by the term "alkyl", may be referred to as "cycloalkyl" and include those with 3 to 10 carbon atoms having single or multiple fused rings. Non-limiting examples of cycloalkyl groups include adamantyl, cyclopropyl, cyclobutyl, cyclopentyl, cyclohexyl, cycloheptyl, cyclooctyl and the like.

The alkyl and cycloalkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamonyl, ester, phosphonyl, phosphinyl, phosphoryl, phosphine, thioester, thioether, acid halide, anhydride, oxime, hydrazine, carbamate, phosphonic acid, phosphate, phosphonate, or any other viable functional group that does not inhibit the biological activity of the compounds of the invention, either unprotected, or protected as necessary, as known to those skilled in the art, for example, as taught in Greene, et al., *Protective Groups in Organic Synthesis*, John Wiley and Sons, Fourth Edition, 2007, hereby incorporated by reference.

(2) Alkenyl refers to both straight and branched carbon chains which have at least one carbon-carbon double bond. In one embodiment of alkenyl, the number of double bonds is 1-3, in another embodiment of alkenyl, the number of double bonds is one. In one embodiment of alkenyl, the number of carbons atoms is 2-20, in other embodiments of alkenyl, the number of carbon atoms is 2-12, 2-10, 2-8 or 2-6. In yet another embodiment of alkenyl, the number of carbon atoms is 2-4. Other ranges of carbon-carbon double bonds and carbon numbers are also contemplated depending on the location of the alkenyl moiety on the molecule;

"$C_2$-$C_{10}$-alkenyl" groups may include more than one double bond in the chain. Examples include, but are not limited to, ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

(3) Alkynyl refers to both straight and branched carbon chains which have at least one carbon-carbon triple bond. In one embodiment of alkynyl, the number of triple bonds is 1-3; in another embodiment of alkynyl, the number of triple bonds is one. In one embodiment of alkynyl, the number of carbons atoms is 2-20, in other embodiments of alkynyl, the number of carbon atoms is 2-12, 2-10, 2-8 or 2-6. In yet another embodiment of alkynyl, the number of carbon atoms is 2-4. Other ranges of carbon-carbon double bonds and carbon numbers are also contemplated depending on the location of the alkenyl moiety on the molecule;

For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

(4) Aryl refers to a $C_6$-$C_{14}$ aromatic carbocyclic ring structure having a single ring or multiple fused rings. In some embodiments, the aryl ring may be fused to a non-aromatic ring, as long as the point of attachment to the core structure is through the aromatic ring. Aryl groups include, but are not limited to, phenyl, biphenyl, and naphthyl. In some embodiments aryl includes tetrahydronaphthyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, arylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkylsulfonyl, haloalkenylsulfonyl, haloalkynylsulfonyl, alkylcarbonyl, haloalkylcarbonyl, alkylamino, alkenylamino, alkynylamino, di(alkyl)amino, di(alkenyl)-amino, di(alkynyl)amino, or $SF_5$. In one embodiment of aryl, the moiety is phenyl, naphthyl, tetrahydronaphthyl, phenylcyclopropyl and indanyl; in another embodiment of aryl, the moiety is phenyl.

(5) Alkoxy refers to —O-alkyl, wherein alkyl is as defined in (1);

(6) Alkoxycarbonyl refers to —C(=O)—O-alkyl, wherein alkoxy is as defined in (5);

(7) Cyclo as a prefix (e.g. cycloalkyl, cycloalkenyl, cycloalkynyl) refers to a saturated or unsaturated cyclic ring structure having from three to eight carbon atoms in the ring the scope of which is intended to be separate and distinct from the definition of aryl above. In one embodiment of cyclo, the range of ring sizes is 4-7 carbon atoms; in another embodiment of cyclo the range of ring sizes is 3-4. Other ranges of carbon numbers are also contemplated depending on the location of the cyclo-moiety on the molecule;

(8) Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl (—$CH_2Cl$), dichloromethyl (—$CHCl_2$), trichloromethyl (—$CCl_3$));

(9) Heterocycle, heterocyclic, heterocyclyl or heterocyclo refers to fully saturated or unsaturated cyclic groups, for example, 4 to 7 membered monocyclic, 7 to 11 membered bicyclic, or 10 to 15 membered tricyclic ring systems, which have at least one heteroatom in the ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

(10) Heteroaryl refers to a monovalent aromatic ring of from 5 to 15 atoms, preferably from 5 to 10 atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple fused rings provided that the point of attachment is through a heteroaryl ring atom. Preferred heteroaryls include pyridyl, piridazinyl, pyrimidinyl, triazinyl, pyrrolyl, quinolinyl, isoquinolinyl, quinazolinyl, quinoxalinnyl, furanyl, thienyl, furyl, imidazolyl, oxazolyl, isoxazolyl, isothiazolyl, pyrazolyl, benzofuranyl, and benzothienyl. Heteroaryl rings may be unsubstituted or substituted by one or more moieties as described for aryl above.

Exemplary monocyclic heterocyclic or heteroaryl groups also include, but are not limited to, pyrrolidinyl, oxetanyl, pyrazolinyl, imidazolinyl, imidazolidinyl, oxazolidinyl, isoxazolinyl, thiazolyl, thiadiazolyl, thiazolidinyl, isothiazolidinyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, and the like.

Exemplary bicyclic heterocyclic groups include, but are not limited to, indolyl, benzothiazolyl, benzoxazolyl, benzodioxolyl, benzothienyl, quinuclidinyl, tetra-hydroisoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include, but are not limited to, carbazolyl, benzidolyl, phenanthrolinyl, acridinyl, phenanthridinyl, xanthenyl and the like.

In a first aspect of the invention, a process for the preparation of 1-arylpyrazole compounds of formula (I) is provided, which avoids the use of hazardous sulfenyl halide reagents:

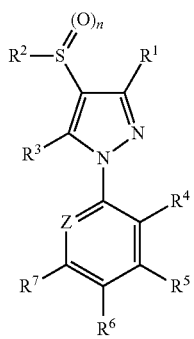

(I)

wherein:
$R^1$ and $R^3$ are each independently hydrogen, alkyl, haloalkyl, cycloalkyl, halocycloalkyl, cyano, hydroxyalkyl, alkoxyalkyl, aminoalkyl, alkylaminoalkyl, dialkylaminoalkyl, alkenyl, alkynyl, formyl, aryl, heteroaryl, heterocyclyl, —$CO_2H$, —$C(O)R^8$, —$C(O)OR^8$, —$C(O)NR^9R^{10}$ or $C(S)NH_2$, wherein each alkyl, cycloalkyl, alkenyl, alkynyl, aryl, heterocyclyl or heteroaryl group may optionally be substituted by one or more of halogen, hydroxy, alkoxy, alkoxyalkoxy, amino, alkylamino, dialkylamino, alkyl or haloalkylthio, alkyl or haloalkylsulfinyl, alkyl or haloalkylsulfonyl, nitro, cyano or $C(S)NH_2$;

$R^2$ is alkyl, haloalkyl, alkenyl, haloalkenyl, alkynyl, haloalkynyl, cycloalkyl or halocycloalkyl;

$R^4$, $R^5$, $R^7$ and $R^{12}$ are each independently hydrogen, halogen, alkyl, haloalkyl, cyano or nitro;

$R^6$ is halogen, alkyl, haloalkyl, alkoxy, haloalkoxy, cyano, nitro, —$C(O)R^{11}$, —$S(O)_mR^{11}$ or $SF_5$;

Z is nitrogen or C—$R^{12}$;

$R^8$ is alkyl, haloalkyl, cycloalkyl or halocycloalkyl;

$R^9$ and $R^{10}$ are independently hydrogen, alkyl, haloalkyl, hydroxy or alkoxy;

$R^{11}$ is alkyl or haloalkyl; and m and n are independently 0, 1 or 2;

which comprises:

i) reacting a disulfide compound of formula (II) with an arylhydrazine of formula (III)

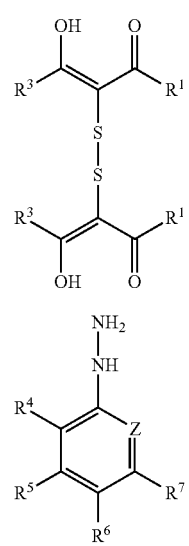

(II)

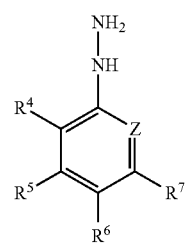

(III)

wherein $R^1$ and $R^3$ are each independently hydrogen, alkyl, haloalkyl, cycloalkyl, halocycloalkyl, hydroxyalkyl, alkoxyalkyl, aminoalkyl, alkylaminoalkyl, dialkylaminoalkyl, alkenyl, alkynyl, formyl, aryl, heteroaryl, heterocyclyl, —$C(O)R^8$, —$C(O)OR^8$, —$C(O)NR^9R^{10}$ or —$C(S)NH_2$, wherein each alkyl, cycloalkyl, alkenyl, alkynyl, aryl, heterocyclyl or heteroaryl group may optionally be substituted by one or more of halogen, hydroxy, alkoxy, alkoxyalkoxy, amino, alkylamino, dialkylamino, alkyl or haloalkylthio, alkyl or haloalkylsulfinyl, alkyl or haloalkylsulfonyl, nitro, cyano or —$C(S)NH_2$; and $R^4$, $R^5$, $R^6$, $R^7$ and Z are as defined for the compound of formula (I), to form a pyrazole disulfide of formula (IV)

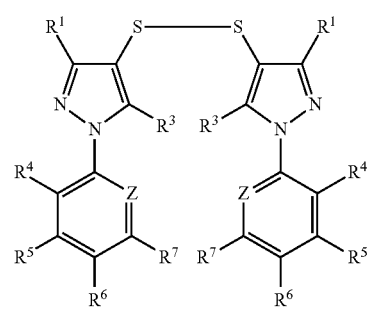

(IV)

wherein $R^1$ and $R^3$ are as described for formula (II) above; and $R^4$, $R^5$, $R^6$, $R^7$ and Z are as defined for the compound of formula (I);

ii) reacting the compound of formula (IV) with a compound of formula (V)

$R^2$-LG (V)

wherein $R^2$ is as defined above for the compound of formula (I) and LG is a leaving group to form a compound of formula (VI), wherein $R^1$, $R^2$, $R^3$, $R^4$, $R^5$, $R^6$, $R^7$ and Z are as defined above for the compound of formula (I)

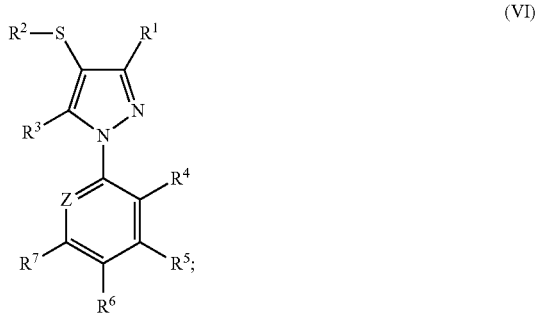

iii) wherein if $R^1$ or $R^3$ in the compound of formula (VI) are —C(O)OR$^8$ or —C(O)NR$^9$R$^{10}$, optionally converting the —C(O)OR$^8$ or —C(O)NR$^9$R$^{10}$ groups to cyano, hydroxyalkyl, aminoalkyl, dialkylaminoalkyl, formyl, —C(O)R$^8$ or —C(S)NH$_2$ via functional group conversion; and iv) optionally oxidizing the group —SR$^2$ to form the compound of formula (I);

wherein the sequence of steps iii) and iv) may be interchanged.

It will be appreciated by persons skilled in the art that the order of the synthetic steps of the processes described herein may be varied and will depend inter alia on factors such as the nature of other functional groups present in a particular substrate, the availability of key intermediates, and the protecting group strategy (if any) to be adopted (see e.g. "Protective Groups in Organic Synthesis (Third Edition)", eds. Greene and Wuts, Wiley-Interscience, (1999)). Clearly, such factors will also influence the choice of reagents for use in the synthetic steps.

Furthermore, it will be appreciated that certain preferred compounds of formula (I) may be prepared by appropriately selecting the groups $R^1$ and $R^3$ in the compound of formula (VII) and the groups $R^4$, $R^5$, $R^6$, $R^7$ and Z in the compound of formula (III). In addition, it will be apparent to those of skill in the art, that certain compounds of formula (I) may be prepared by further elaborating the functional groups present in the compounds, for example, by converting an ester —C(O)OR$^8$ at the 3- or 5-position of the pyrazole ring to a carboxylic acid, a hydroxymethyl group, an amide and the like using well known functional group transformations. Furthermore, as described in U.S. Pat. No. 7,759,381 (incorporated herein by reference), an ester group or amide group may be converted to a cyano group. For example, an ester group may be subjected by hydrolysis to the carboxylic acid, followed by formation of an amide and treatment of the amide with a dehydrating agent such as SOCl$_2$ to form the cyano group. The group —C(S)NH$_2$ may be formed from the corresponding cyano group by treatment with hydrogen sulfide, as described in U.S. Pat. Nos. 6,265,430 and 6,518,296, both incorporated herein by reference in their entirety.

In one embodiment, the process of the invention may be used to prepare compounds of formula (I) wherein $R^1$ is cyano, —C(O)OR$^8$, —C(O)NR$^9$R$^{10}$ or —C(S)NH$_2$.

In another embodiment, the process of the invention may be used to prepare compounds of formula (I) wherein $R^3$ is $C_1$-$C_6$ alkyl, optionally substituted by one or more halogen atoms.

In still another embodiment, the process of the invention may be used to prepare compounds of formula (I) wherein $R^3$ is methyl or ethyl optionally substituted with one to five halogen atoms.

In another embodiment, the process of the invention may be used to prepare compounds of formula (I) wherein $R^3$ is methyl, —CH$_2$F, —CHF$_2$, CF$_3$, ethyl, —CHFCH$_3$, —CF$_2$CH$_3$, —CF$_2$CF$_3$, or —CHFCF$_3$.

In another embodiment, the process of the invention may be used to prepare compounds of formula (I) where $R^2$ is $C_1$-$C_3$ alkyl or $C_1$-$C_3$ haloalkyl.

In another embodiment, the process of the invention may be used to prepare compounds of formula (I) where $R^2$ is methyl, ethyl, —CF$_3$, —CCl$_2$F or —CF$_2$Cl.

In another embodiment, the process of the invention may be used to prepare compounds of formula (I) wherein $R^1$ is cyano, —C(O)OR$^8$, —C(O)NR$^9$R$^{10}$ or C(S)NH$_2$; $R^3$ is $C_1$-$C_6$ alkyl, optionally substituted by one or more halogen atoms; and $R^5$ and $R^7$ are each hydrogen.

In another embodiment, the process of the invention may be used to prepare compounds of formula (I) wherein $R^1$ is cyano, —C(O)OR$^8$ or —C(O)NR$^9$R$^{10}$; $R^3$ is methyl or ethyl optionally substituted by one to five halogen atoms; $R^5$ and $R^7$ are each hydrogen; and $R^4$ is halogen.

In another embodiment, the process of the invention may be used to prepare compounds of formula (I) wherein $R^1$ is cyano, —C(O)OR$^8$ or —C(O)NR$^9$R$^{10}$; $R^3$ is methyl or ethyl optionally substituted by one to five halogen atoms; $R^2$ is $C_1$-$C_3$ alkyl or $C_1$-$C_3$ haloalkyl; $R^5$ and $R^7$ are each hydrogen; Z is C—R$^{12}$; and $R^4$ and $R^{12}$ are chloro or fluoro.

In still another embodiment, the process of the invention may be used to prepare compounds of formula (I) wherein $R^1$ is cyano, —C(O)OR$^8$, —C(O)NR$^9$R$^{10}$ or C(S)NH$_2$; $R^3$ is methyl, —CH$_2$F, —CHF$_2$, CF$_3$, ethyl, —CHFCH$_3$, —CF$_2$CH$_3$, —CF$_2$CF$_3$, or —CHFCF$_3$; and $R^2$ is methyl, ethyl, —CF$_3$, —CCl$_2$F or —CF$_2$Cl.

In a preferred embodiment, the process of the invention may be used to prepare compounds of formula (I) wherein $R^1$ is cyano, —C(O)OR$^8$ or —C(O)NR$^9$R$^{10}$; $R^3$ is methyl; and $R^2$ is CF$_3$, —CCl$_2$F or —CF$_2$Cl; $R^5$ and $R^7$ are each hydrogen; Z is C— R$^{12}$; and $R^4$ and $R^{12}$ are chloro or fluoro.

The disulfide compounds of formula (II) may be prepared by the reaction of a 1,3-dicarbonyl compound of formula (VII):

wherein $R^1$ and $R^3$ are as defined for the compound of formula (II), with a disulfide reagent having a leaving group on each sulfur atom, as in the formula LG-S—S-LG, wherein LG is a leaving group. In one embodiment, the disulfide reagent is a disulfide dihalide reagent. In a preferred embodiment, the disulfide dihalide reagent is disulfide dichloride (Cl—S—S—Cl) or disulfide dibromide (Br—S—S—Br).

The 1,3-dicarbonyl compounds of formula (VII) are well known in the art for a variety of different $R^1$ and $R^3$ groups, including compounds where $R^1$ and/or $R^3$ are alkyl, haloalkyl, —C(O)OR$^8$, —C(O)NR$^9$R$^{10}$, alkenyl, alkynyl, aryl, heterocyclyl and heteroaryl. Further, 1,3-dicarbonyl compounds substituted at the 2-position are also known in the art and have been described, for example, in Chem. Ber. 1973, 106, 1418-14-22; J. Org. Chem., 1973, 38, 2809-2813; J. Org.

Chem. 1981, 46, 153-157; J. Org. Chem. 1984, 49, 3494-3498; and U.S. Pat. No. 3,742,046, which is incorporated herein by reference. Table 1 below provides a very limited survey of the vast number of 1,3-diketone compounds of formula (VII) that are known in the art, referenced by their CAS Registry Number.

TABLE 1

Non-limiting Compounds of Formula (VII)

| $R^1$ | $R^3$ | CAS No. |
|---|---|---|
| $CF_3$ | methyl | 367-57-7 |
| $CF_2CF_3$ | methyl | 356-40-1 |
| $CO_2H$ | ethyl | 4383-93-1 |
| $CO_2H$ | methyl | 5699-58-1 |
| $CO_2H$ | n-propyl | 60415-20-5 |
| $CO_2Me$ | methyl | 20577-61-1 |
| $CO_2Et$ | ethyl | 13246-52-1 |
| $CONH_2$ | methyl | 725240-73-3 |
| $CONH_2$ | Ph | 66287-48-4 |
| $CONH_2$ | t-butyl | 362685-25-4 |
| CONHPh | methyl | 503300-35-4 |
| methyl | —C≡$CH_2$ | 52204-69-0 |
| methyl | —C($CH_3$)=$CH_2$ | 20583-46-4 |
| methyl | —$CH_2$—CH=$CH_2$ | 53754-66-8 |
| methyl | —≡—H | 92836-61-8 |
| methyl | —≡—Me | 1259209-00-1 |
| methyl | —≡—Ph | 115546-08-2 |
| methyl | Benzimidazol-2-yl | 106-971-56-6 |
| $CF_3$ | N-methylimidazol-2-yl | 942223-89-4 |
| Ph | Benzimidazol-2-yl | 840523-77-5 |
| Cyclopropyl | Benzimidazol-2-yl | 1284702-45-9 |
| methyl | 3-pyridinyl | 3594-37-4 |
| Methyl | Cyclohexyl | 15972-15-3 |

Furthermore, the compounds of formula (VII) may be prepared by the application or adaptation of known methods described in the chemical literature. Methods for the preparation of compounds of formula (VII) are well known in the art, and a large number of compounds with different substitution pattern are attainable (see for example, Levine, R. et al., *JACS*, 1945, 67, pp. 1510-1512 and Fargeas, V. et al., *Tetrahedron*, 2004, 60, 10359-10364).

In some embodiments, the reaction between the 1,3-dicarbonyl compound of formula (VII) and the disulfide reagent LG-S—S-LG, including a disulfide dihalide reagent, may be conducted in the presence of a base. In other embodiments, the reaction between the 1,3-dicarbonyl compounds of formula (VII) and the disulfide reagent LG-S—S-LG may be conducted in the presence of a Lewis acid. Suitable bases include alkali metal or alkaline earth carbonates, bicarbonates, hydroxides and alkoxides; and organic amine bases including, but not limited to, triethylamine, diisopropylethylamine, 1,5-diazabicyclo[4.3.0]non-3-ene (DBN); 1,4-diazabicyclo[2.2.2]octane (DABCO); 1,8-diazabicyclo[5.4.0]undec-7-ene (DBU), and the like; and alkali metal amide bases including, but not limited to, lithium diisopropyl amide (LDA), sodium or lithium hexamethyldisilazane, and the like.

Lewis acids that may be used in the reaction of the compound of formula (VII) with a group LG-S—S-LG, including a disulfide dihalide reagent, include copper salts including, but not limited to, $Cu(OAc)_2$, $TiCl_4$, $BF_3$-etherate, scandium III triflate, $ZnCl_2$, Lanthanium III trifluoromethanesulfonate, and the like. A particularly preferred Lewis acid is $Cu(OAc)_2$. Other suitable Lewis acids may also be used to effect the reaction.

The reaction may be performed at any temperature range in which a suitable reaction conversion is attained without excessive by-product formation. Reaction temperatures include, but are not limited to, of about −78° C. to the boiling point of the solvent used, including about −78° C. to about 110° C.; about −78 to about 80° C.; about −78° C. to about 50° C.; about −78° C. to about 30° C.; about −78° C. to about 20° C.; or about −78° C. to about 0° C. In other embodiments, the reaction is run at about 0° C. to about 50° C.; about 0° C. to about 30° C.; or about ° C. to about 20° C.

In certain preferred embodiments when a base is used, the reaction is started at a colder temperature and then warmed to ensure a complete reaction. In other embodiments, the reaction temperature may be held constant for a period of time until as suitable reaction conversion is attained. One of skill in the art would be able to determine the optimum reaction temperature to attain a suitable reaction rate while keeping impurity formation to a minimum by monitoring the purity of and conversion of the reaction.

The reactions may be conducted in the presence of a solvent that does not interfere or react with the compound of formula (VII) or the disulfide reagent, such as a non-reactive organic solvent. Non-reactive organic solvents include, but are not limited to aprotic organic solvents including aromatic solvents such as toluene, xylene, ethylbenzene, anisole, and the like; chlorinated solvents such as dichloromethane and chloroform; ethers such as tetrahydrofuran, 2-methyltetrahydrofuran, dioxane, ethyl ether, methyl tert-Butyl ether, and the like; ester solvents including alkyl esters such as ethyl acetate, n-propylacetate, isopropyl acetate, n-butyl acetate, isobutyl acetate, and the like. In some embodiments, the reaction may be performed without a solvent or using the base as both a solvent and base.

The compounds of formula (II) obtained from the reaction of the compound of formula (VII) with a disulfide reagent LG-S—S-LG may be isolated and purified by methods known in the art, or may be used directly without isolation and/or purification. In one embodiment, the compound of formula (II) is purified by trituration or crystallization from a suitable solvent or by chromatography.

Similarly, the compounds of formula (III) have been previously described in the art. For example, the preparation of arylhydrazine compounds of formula (III) have been described in U.S. Pat. Nos. 4,909,832; 4,810,720; 4,127,575; 3,609,158; 5,256,364; in U.K. Patent Publication Nos. GB1469610 and GB2136427; and in J. Chem. Soc. C, 1971, 167-174 (all incorporated herein by reference), among other places. The arylhydrazine compounds of formula (III) may also be prepared by adaptation of known processes (e.g. as described in Advanced Organic Chemistry, Third Edition by Jerry March, Wiley-Interscience, New York).

The reaction of the compound of formula (III), or a salt thereof, with the compound of formula (II) to yield a compound of formula (IV) may be conducted in an organic solvent at a temperature of between about −20° C. to about 100° C. Typically, the reaction may be conducted at a temperature of between about 0° C. to about 70° C., about 0° C. to about 50° C., about 0° C. to about 30° C., or about 0° C. to about 20° C. More typically, the reaction may be carried out at a temperature of about −5° C. to about 5° C., about −5° C. to about 10° C., or 0° C. to about 10° C. In other embodiments, the reaction is run at a temperature of about 15° C. to about 25° C., or about 20° C. to about 30° C.

The reaction may be carried out in a variety of organic solvents including, but not limited to, $C_1$-$C_4$ alcohol solvents such as ethanol, methanol or isopropanol; halogenated solvents such as dichloromethane, chloroform, and the like; aromatic solvents such as toluene, xylene, ethylbenzene, and the like, ether solvents such as tetrahydrofuran, ethyl ether and the like; amide solvents such as dimethylformamide (DMF), dimethylacetamide (DMA) and the like.

In certain embodiments, the reaction is preferably conducted in the presence of an acid catalyst or a Lewis acid catalyst. Suitable acids include, but are not limited to, carboxylic acids such as formic acid, acetic acid, trifluoroacetic acid, trichloroacetic acid, benzoic acid, fumaric acid and the like; mineral acids including hydrochloric acid, sulfuric acid and phosphoric acid; sulfonic acids including methanesulfonic acid, trifluoromethanesulfonic acid, p-toluenesulfonic acid, and the like. Suitable Lewis acid catalysts include, but are not limited to $TiCl_4$, $BF_3$-etherate, $Cu(OAc)_2$, scandium III triflate, $ZnCl_2$, Lanthanium III trifluoromethanesulfonate, and the like.

The compounds of formula (IV) may be isolated and purified by standard techniques known in the art such as crystallization from a suitable solvent or by chromatography. In some embodiments, depending on the substitution pattern of the compounds of formula (II), the reaction may yield regioisomeric compounds (e.g. if $R^1 \neq R^3$). In these circumstances, it will typically be useful to purify the product before carrying out further reactions. However, in certain other embodiments where the amount of the undesired isomer is acceptable, it may be preferable to process the compounds of formula (IV) further to the next step directly to avoid costly isolation and/or purification steps. Furthermore, certain substitution patterns and conditions may be found that provide one regioisomer of the compound of formula (IV) as the major product.

Pyrazole disulfide compounds have been described in, for example, Alabaster et al., Journal of the Chemical Society, 1965, pp. 4974-4978; Journal of the Chemical Society —C, 1970, pp. 78-81; and Journal of the Chemical Society, Perkin Trans. 1, 1976, pp. 428-433. Compounds of formula (IV) where $R^3$ is —$NH_2$ have been described in the art, for example, in U.S. Pat. Nos. 4,810,720; 4,804,675; 5,283,337; 5,232,940; 6,881,848, all incorporated herein by reference, and Clavel et al., *J. Chem. Soc. Perkin Trans.* 1, 1992, pp. 3371-3375. As described in these publications, the compounds of formula (IV) where $R^3$ is $NH_2$ may be prepared from the corresponding 4-thiocyanato-5-aminopyrazole compounds by reaction with aqueous hydrochloric acid in a solvent such as ethanol. The 4-thiocyanato-5-aminopyrazole compounds are known (see for example Farmaco Ed. Sci. 1983, 38, 274-282) or obtained by reacting the 4-unsubstituted-5-aminopyrazole compounds with ammonium thiocyanate in the presence of bromine and acetic acid at temperatures of between −20° C. and 20° C.

However, Applicants have found that the disulfide compounds of formula (IV) where $R^3$ at the 5-position of the pyrazole ring is a carbon-linked group (e.g. where the group $R^3$ is linked to the pyrazole by a carbon atom) are not readily obtainable by known methods, particularly when the 3-position contains a carbonyl or cyano substituent. Furthermore, 4-thiocyanato pyrazole compounds that are substituted with a carbon-linked group at the 5-position, particularly those having a carbonyl group or a cyano group at the 3-position, from which the corresponding pyrazole disulfide compounds are prepared, are also not readily prepared by the reaction conditions reported in the art. Thus, the preparation of the compounds of formula (IV) of the invention is not straight forward, and access to these compounds by known methods is problematic.

The compounds of formula (IV) where $R^3$ is $NH_2$ may be converted to the compound of formula (I) where $R^3$ is $NH_2$, $R^2$ is perfluoroalkyl and n is 0 by reacting the compounds with a perfluoroalkyl halide in the presence of a reducing agent. This process is described, for example, in U.S. Pat. Nos. 4,810,720; 4,804,675; 5,283,337; 5,232,940; 6,881,848, all incorporated herein by reference, and Clavel et al., *J. Chem. Soc. Perkin Trans.* 1, 1992, pp. 3371-3375. However, Applicants have found that the reaction of a compound of formula (IV) where $R^3$ is not an amino group, particularly compounds where $R^1$ is a carbonyl group or cyano, does not proceed using the reaction conditions described in the prior art to produce the compounds of formula (I). Thus, the intermediary of disulfide compounds of formula (IV) does not provide easy access to compounds of formula (I) when $R^3$ is not an amino group. Accordingly, aspect 1 of the present invention provides improved processes for the synthesis of compounds of formula (I) where $R^3$ is a carbon-linked functional group. These compounds are not easily accessible using the synthetic processes known in the art for phenylpyrazole compounds.

However, Applicants have surprisingly found that disulfide compounds of formula (IV) where $R^3$ is functional group linked to the pyrazole ring by a carbon atom provide compounds of formula (I) when the reaction is carried out using a compound of formula (V) $R^2$-LG, preferably where LG is a halogen atom, in the presence of tetrakis(dimethylamino) ethylene (TDAE) as a reducing agent.

A second aspect of the invention provides a process for the preparation of compounds of formula (IB) which avoids the use of hazardous sulfenyl halide reagents:

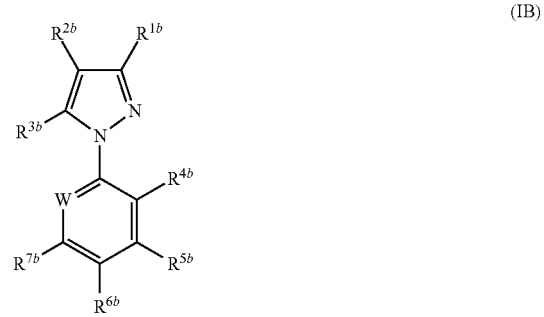

(IB)

wherein:
$R^{1b}$ is hydrogen, cyano, halogen, $R^{8b}$, formyl, —$CO_2H$, —$C(O)R^{8b}$, —$C(O)OR^{8b}$, —$C(O)NR^{9b}R^{10b}$ or $C(S)NH_2$;
$R^{2b}$ is $R^{8b}$ or —$S(O)_m R^{11b}$;
$R^{3b}$ is alkyl, haloalkyl, cycloalkyl, halocycloalkyl, alkenyl, alkynyl, aryl, heterocyclyl, heteroaryl, $R^{8b}NH$, $(R^{8b})_2N$, $R^{8b}O$, $R^{8b}S$ or $R^{8b}C(O)CH_2$—, wherein each alkyl, cycloalkyl, alkenyl, alkynyl, aryl, heterocyclyl or heteroaryl group may optionally be substituted by one or more of halogen, hydroxy, alkoxy, alkoxyalkoxy, amino, alkylamino, dialkylamino, nitro, cyano or —$C(S)NH_2$;
$R^{4b}$, $R^{5b}$, $R^{7b}$ and $R^{13b}$ are each independently hydrogen, halogen, alkyl, haloalkyl, cyano or nitro;
$R^{6b}$ is halogen, alkyl, haloalkyl, alkoxy, haloalkoxy, cyano, nitro, —$C(O)R^{12b}$, —$S(O)_n R^{12b}$ or $SF_5$;
W is nitrogen or C—$R^{13b}$;
$R^{8b}$ is alkyl, haloalkyl, cycloalkyl, halocycloalkyl, hydroxyalkyl, alkenyl, haloalkenyl, alkynyl, haloalkynyl, aryl, heterocyclyl or heteroaryl;
$R^{9b}$ and $R^{10b}$ are independently hydrogen, alkyl, haloalkyl, hydroxy or alkoxy;
$R^{11b}$ is alkyl, haloalkyl, alkenyl, haloalkenyl, alkynyl, haloalkynyl, cycloalkyl or halocycloalkyl;
$R^{12b}$ is alkyl or haloalkyl;
m is 0, 1 or 2; and
n is 0, 1 or 2;

which comprises:
(i) reacting a compound of formula (IIB):

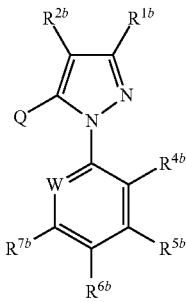

(IIB)

wherein $R^{1b}$, $R^{2b}$, $R^{4b}$, $R^{5b}$, $R^{6b}$, $R^{7b}$ and W are as defined above for the compound of formula (IB) and Q is iodo, bromo, chloro or a haloalkylsulfonate group (—OS(O)$_2$haloalkyl) including, but not limited to, triflate (trifluoromethanesulfonate);
with a compound of formula (IIc) or (IId):

R—M         (IIc)

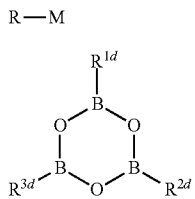

(IId)

wherein R, $R^{1d}$, $R^{2d}$ and $R^{3d}$ are independently alkyl, haloalkyl, cycloalkyl, halocycloalkyl, alkenyl, alkynyl, aryl heterocyclyl or heteroaryl, wherein each alkyl, cycloalkyl, alkenyl, alkynyl, aryl, heterocyclyl or heteroaryl group may optionally be substituted by one or more of halogen, hydroxy, alkoxy, alkoxyalkoxy, amino, alkylamino, dialkylamino, nitro, cyano or —C(S)NH$_2$; M is MgX, ZnX, RZn, BY$_2$, BF$_3$ or SnR'$_3$; X is iodo, bromo or chloro; Y is OH or alkoxy, or each Y may be an alkoxy group which is part a glycol derivative Y—(CR"R'")$_a$—Y where R" and R'" are independently hydrogen or C$_1$-C$_3$ alkyl and a is 2, 3 or 4; and R' is alkyl or haloalkyl;
or
reacting the compound of formula (IIB) with $R^{8b}$NH$_2$, ($R^{8b}$)$_2$NH, $R^{8b}$OH, $R^{8b}$SH or an enolate anion $R^{8b}$C(O)CH$_2^-$, wherein $R^{8b}$ is as defined for the compound of formula (IB);
in the presence of a transition metal catalyst to form the compound of formula (IB);
(ii) wherein if $R^{1b}$ in the compound of formula (IB) is —C(O)OR$^{8b}$ or —C(O)NR$^{9b}$R$^{10b}$, optionally converting the —C(O)OR$^{8b}$ or —C(O)NR$^{9b}$R$^{10b}$ groups to cyano, hydroxyalkyl, aminoalkyl, dialkylaminoalkyl, formyl, —C(O)R$^{8b}$ or —C(S)NH$_2$, wherein $R^{8b}$, $R^{9b}$ and $R^{10b}$ are as defined above for formula (IB), via functional group conversion; and
(iii) wherein if $R^{2b}$ is —S(O)$_m$R$^{11b}$, optionally oxidizing the group —S(O)$_m$R$^{11b}$ where $R^{11b}$ is as defined above for the compound of formula (IB) and m is 0 or 1, to form the compound of formula (IB);
wherein the sequence of steps ii) and iii) may be interchanged.

Compounds of formula (IIB), wherein Q is Br, Cl or I are known in the art, for example, in EP 0 295 117 and U.S. Pat. No. 5,232,940, both incorporated herein by reference. In addition, these compounds may be prepared from a 5-amino-substituted arylpyrazole compound of formula (IIIB) shown below.

In one embodiment of the process, the compound of formula (IIB) wherein Q is I, Br or Cl is prepared by reacting a compound of formula (IIIB):

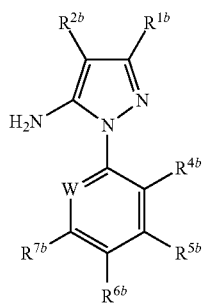

(IIIB)

wherein $R^{1b}$, $R^{2b}$, $R^{4b}$, $R^{5b}$, $R^{6b}$, $R^{7b}$ and W are as defined above for the compound of formula (IB), with a source of Br, Cl or I in the presence of a nitrite compound T-ONO where T is hydrogen or alkyl, or a salt thereof. Examples of nitrite compounds T-ONO include, but are not limited to, nitrite salts such as NaNO$_2$ and alkyl nitrites such as isopentyl nitrite, tert-Butyl nitrite, and the like.

A variety of 5-amino pyrazole compounds are known in the art, and the synthesis of these compounds has been widely reported. For example, compounds of formula (IIIB) may be prepared by the application or adaptation of known methods (i.e. methods heretofore used or described in the chemical literature): generally pyrazole ring formation followed where necessary by changing substituents; or methods described in one or more of U.S. Pat. Nos. 5,232,940; 5,618,945; 5,306,694; 4,772,312; 4,804,675; 4,614,533; 3,402,308; 6,620,943; EP 0 295 117 and WO 2009/077853, all incorporated herein by reference in their entirety.

The conversion of an amino-substituted aryl compound to a halogen-substituted aryl compound via an intermediate diazonium salt is well known in the art. One well-known process for this transformation is called the Sandmeyer Reaction (see, for example Advanced Organic Chemistry, Third Edition, by Jerry March, Wiley-Interscience, New York; Butler, R. N., for diazotization of amines see *Chemical Reviews*, 1975, vol. 75(2), 241-257). The Sandmeyer reaction involves the treatment of an aryl diazonium salt with cuprous chloride to obtain the corresponding aryl chloride. The conversion of a diazonium group to a halide can also be carried out without copper using HBr or HCl and is called the Gatterman reaction. Aryl bromides and aryl chlorides may also be prepared in one step from the corresponding amine by various methods including the treatment of the amine with a nitrite reagent and CuCl$_2$ or CuBr$_2$. This corresponds to a diazonium formation from the amine followed by conversion of the intermediate salt to the desired aryl halide. Aryl iodides may also be prepared from the corresponding aryl diazonium salt by reaction with a suitable iodide source including, but not limited to, KI, NaI, LiI and the like.

Certain reactions with pyrazole compounds have also been described in the literature. For example, Colomer et al. describe the synthesis of pyrazolo[3,4-d][1,2,3]triazin-4- ones by the diazotization of 5-amino-1H-pyrazole-4-carbonitriles (Colomer and Moyano, Tett. Lett., 2011, 52(14), 1561-1565). Yamamoto et al., describe the synthesis of 5-chloropyrazole compounds from the corresponding 5-aminopyrazole compounds (J. Heterocyclic Chemistry, 1991, 28(6), 1545-1547). Gorja et al., describe the preparation of 5-iodo-pyrazole-4-carboxylic acid compounds from the corresponding 5-amino pyrazole compound followed by palladium-catalyzed alkynylation (Gorja et al., Beilstein Journal of Organic Chemistry, 2009, 5(64)). However, the pyrazole compounds described in these publications have distinct substitution patterns from the phenylpyrazole compounds of formula (IIIB).

The amount of the nitrite compound T-ONO used in the process may be varied to achieve the best conversion of the compound of formula (IIIB) to the compound of formula (IIB). In one embodiment, about 0.8 to about 5 equivalents of the nitrite compound per mole of the compound of formula (IIIB) may be used. In another embodiment, about 1.0 to about 4 equivalents may be used. In still other embodiments, about 1.0 to about 3.0 equivalents of the nitrite compound may be used. In yet another embodiment, about 2.0 equivalents of the nitrite compound may be used.

In one embodiment, the source of Br, Cl or I will be HBr, HCl or HI. When a hydrohalide acid is used as the halide source, the amount of the acid may be adjusted to obtain the best conversion of the compound of formula (IIIB) to the compound of formula (IIB). In one embodiment, the hydrohalide acid used will be an aqueous solution of the acid. In another embodiment, the amount of acid used will be from about 1 equivalent to about 20 equivalents per mole of the compound of formula (IIIB). In another embodiment, about 1 equivalent to about 10 equivalents of the acid will be used. In still other embodiments, about 2 equivalents to about 8 equivalents of the acid will be used. In yet another embodiment, about 3 equivalents to about 7 equivalents of the acid will be used. In a particular embodiment of the invention, about 5 equivalents of the acid will be used.

In another embodiment, the source of Br, Cl or I will be bromine, chlorine or iodine.

In another embodiment, the source of Br, Cl or I will be an alkali metal salt of the acid such as the sodium, lithium, cesium or potassium salt. In one embodiment, sodium, lithium, potassium or cesium bromide may be used. In another embodiment, sodium, lithium, potassium or cesium chloride may be used. In still another embodiment, sodium, lithium, potassium or cesium iodide may be used. The amount of the alkali metal salt used may be varied. In one embodiment, about 0.5 to about 10 equivalents of the salt per mole of the compound of formula (IIIB) may be used. In another embodiment, about 0.5 to about 5 equivalents of the salt may be used. In still another embodiment, about 1.0 to about 3 equivalents of an alkali metal salt may be used. For example, in one embodiment of the invention, it was found that addition of 1.2 equivalents of KBr as the bromide source to the reaction of a compound of formula (IIIB) (1 eq.) with 3 equivalents of $NaNO_2$ and 5 eq. of HBr resulted in 86.5% product formation after 30 min. at 0° C. and 5 hours at 50° C.

In still another embodiment, the source of Br, Cl or I will be the copper (I) or copper (II) chloride, bromide or iodide. The copper (I) or (II) halide may be used in catalytic amounts or in stoichiometric amounts per mole of the compound of formula (IIIB). In one embodiment, about 0.2 equivalents to about 2 equivalents of a copper halide may be used. In another embodiment, about 0.3 to about 2 equivalents or about 0.3 to about 1.5 equivalents of copper (I) or copper (II) halide may be used in the process. For example, 0.3 eq. of CuBr was found to effectively provide the desired product with 2 eq. of $NaNO_2$ and 5 eq. of HBr. Similarly, 1 eq. of CuBr was found to provide the desired product. In other embodiments, the use of 0.5 eq. of CuBr or $CuBr_2$ was found to provide efficient conversion to the desired product.

In still another embodiment, the source of Br, Cl or I will be bromoform, chloroform or iodoform.

In another embodiment, the reaction is conducted with a combination of different sources of Br, Cl or I. For example, the reaction may be conducted with copper (I) halide or copper (II) halide and alkali metal halide salt. In one embodiment, the reaction of the compound of formula (IIIB) to provide the compound of formula (IIB) is conducted with $CuBr_2$ and/or CuBr and KBr. In another embodiment, the reaction is conducted with $CuBr_2$ and/or CuBr and NaBr. In yet another embodiment, the reaction is conducted with $CuBr_2$ and/or CuBr and LiBr. In another embodiment, the reaction is conducted with $CuBr_2$ and/or CuBr and CsBr.

In one embodiment, the reaction of the compound of formula (IIIB) to provide the compound of formula (IIB) is conducted with $CuCl_2$ and/or CuCl and KCl. In another embodiment, the reaction is conducted with $CuCl_2$ and/or CuCl and NaCl. In yet another embodiment, the reaction is conducted with $CuCl_2$ and/or CuCl and LiCl. In another embodiment, the reaction is conducted with $CuCl_2$ and/or CuCl and CsCl. In yet one embodiment, the reaction of the compound of formula (IIIB) to provide the compound of formula (IIB) is conducted with $CuI_2$ and/or CuI and KI. In another embodiment, the reaction is conducted with $CuI_2$ and/or CuI and NaI. In yet another embodiment, the reaction is conducted with $CuI_2$ and/or CuI and LiI. In another embodiment, the reaction is conducted with $CuI_2$ and/or CuI and CsI.

In one embodiment of the invention, the conversion of the compound of formula (IIIB) to the compound of formula (IIB) will use a combination of about 2 to about 5 equivalents of T-ONO together with about 3 to about 8 equivalents of a hydrohalide acid HX (where X is Br, Cl or I) per mole of the compound of formula (IIIB). In another embodiment, the process will use about 3 to about 5 equivalents of T-ONO and about 3 to about 6 equivalents of HX. In still another embodiment, the process will use about 3 equivalents of T-ONO and about 3 equivalents of HX. In another embodiment, the process will use about 3 equivalents of T-ONO and about 5 equivalents of HX.

The diazonium salt formation-halogenation reaction may be performed at any temperature range in which a suitable reaction conversion is attained without excessive by-product formation. Reaction temperatures include, but are not limited to, of −78° C. to the boiling point of the solvent used, including about −78° C. to 80° C., about −20° C. to about 80° C., about −10° C. to about 60° C. or about 0° C. to about 50° C. In other embodiments, the reaction is run at about 0° C. to about 20° C., about 0° C. to about 30° C., or about 0° C. to about 40° C. In yet other embodiments, the reaction may be run at a temperature of about 20° C. to about 80° C., about 30° C. to about 60° C. or about 40° C. to about 60° C. In one embodiment, the reaction is run at about 50° C.

It will be understood that it may be preferable in certain embodiments to start the reaction at lower temperatures and then warm the mixture to achieve a reasonable conversion rate. For example, it may be desired to add the reagents at low temperatures, such as less than about ambient temperature, including about 0° C., and then to warm up the reaction mixture to a suitable temperature range (such one of the temperature ranges above, including about 50° C.) to improve the conversion rate and to achieve a suitable reaction conversion.

One of skill in the art would be able to determine the optimum reaction temperature to attain a suitable reaction rate while keeping impurity formation to a minimum by monitoring the composition of the reaction mixture and conversion of the reaction as the reaction progresses. This may be done using standard chromatographic techniques such as high pressure liquid chromatography (HPLC) and the like.

In some embodiments, the reactions may be conducted in the presence of a solvent that does not interfere with the reaction or react with the starting materials, product or reagents. Useful solvents include non-reactive and/or non-nucleophilic organic solvents known in the art. Non-nucleophilic solvents include, but are not limited to, hydrocarbon solvents, aromatic solvents, ethers, halogenated solvents, ester solvents, ketone solvents, amide solvents, nitrile solvents, and the like. Hydrocarbon solvents include heptane, cyclohexane, methylcyclohexane, isooctane, and the like, Aromatic solvents include, but are not limited to, toluene, xylene, ethylbenzene, anisole, and the like. Ethers include, but are not limited to, dioxane, tetrahydrofuran, 2-methyltetrahydrofuran, ethyl ether, methyl tert-butyl ether, butyl ether, and the like. Ester solvents include alkyl esters such as ethyl acetate, n-propyl acetate, isopropyl acetate, n-butyl acetate, isobutyl acetate, and the like. Nitrile solvents include acetonitrile and the like. Ketone solvents include acetone, methyl ethyl ketone, methyl isobutyl ketone, methyl isopropyl ketone, and others. Amide solvents include dimethylformamide, dimethylacetamide, N-methylpyrrolidone, and the like.

In another embodiment, compounds of Formula (IIB) wherein Q is haloalkylsulfonate may be formed by reaction of a compound of formula (IVB) shown below having, a hydroxyl group at the 5-position, wherein variables $R^{1b}$, $R^{2b}$, $R^{4b}$, $R^{5b}$, $R^{6b}$, $R^{7b}$ and W are as defined above for the compound of formula (IB), with a compound of formula $R^T S(O)_2$-L, where $R^T$ is a haloalkyl group and L is a leaving group.

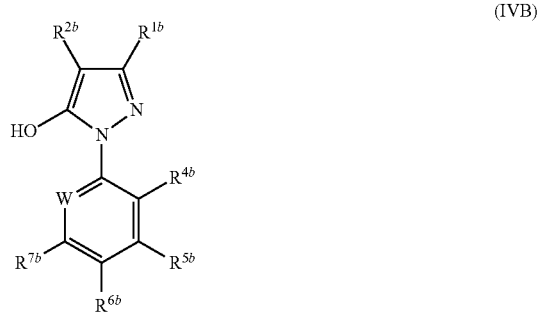

(IVB)

Phenylpyrazole compounds having a 5-hydroxy group on the pyrazole ring are known in the art, for example, in WO 01/40195, U.S. Pat. No. 6,569,886, EP 0 385 809 and U.S. Pat. No. 5,047,550, all incorporated herein by reference. Furthermore, phenylpyrazole compounds having a 5-hydroxyl group at the 5-position of the pyrazole ring may be prepared by treating an intermediate diazonium salt with water in an acidic medium (see Advanced Organic Chemistry, Third Edition, by Jerry March, Wiley-Interscience, New York, pp. 601). Of course, other methods of preparing the 5-hydroxyl-substituted compound may be used.

In some embodiments, L may be a triflate group —OS(O)$_2$CF$_3$. Suitable reagents include, but are not limited to, trifluoromethanesulfonic acid anhydride, N-Phenyl-bis (trifluoromethane)sulfonimide, N-(5-Chloro-2-pyridyl)bis (trifluoromethane)sulfonimide, 2-chloropyridium triflate (including on a resin support) and N-(4-tert-Butylphenyl)bis (trifluoromethanesulfonimide, and the like.

The reaction of the compound of formula (IVB) with $R^T S(O)_2$-L may be conducted in a suitable non-reactive solvent including the non-reactive hydrocarbon solvents, aromatic solvents, ethers, halogenated solvents, ester solvents, ketone solvents, amide solvents, nitrile solvents, and the like, provided above.

The reaction may be carried out at a suitable temperature to achieve the desired conversion to the product including, but not limited to, −78° C. to the boiling point of the solvent. Suitable temperature ranges may include, but are not limited to, about −78° C. to 100° C., about −78° C. to about 80° C., about −78° C. to about 50° C., about −78° C. to about 30° C., about −78° C. to about 20° C., about −78° C. to 0° C., about −78° C. to about −20° C. In other embodiments, the reaction is run at about −20° C. to about 20° C., about −20° C. to about 10° C. or about −20° C. to about 0° C. As discussed above, it will be understood that it may be preferable in certain embodiments to start the reaction at lower temperatures and then warm the mixture to achieve a reasonable conversion rate.

After the reaction for the compound of formula (IIIB) to form the compound of formula (IIB) is complete, the reaction mixture may be worked up to quench the reagents and purify the desired product from the reaction mixture. Any suitable work-up procedure known in the art may be used to remove quench and remove excess reagents and to isolate the product. Suitable work-up procedures for reactions of an aryl or heteroaryl amine to produce the corresponding halide are known in the art and one of skill in the art will be able to determine a suitable procedure.

In one embodiment, the reaction mixture is concentrated to remove excess reaction solvent and/or replace the reaction solvent with another solvent for purification and isolation of the product. For example, it may be desirable to replace a solvent that is miscible with water with a non-miscible solvent so that the mixture can be extracted with water to remove water-soluble components. Thus, in one embodiment the reaction mixture is distilled to remove a portion of the reaction solvent and a second non-water miscible solvent is added. Non-water miscible solvents are well known in the art and include hydrocarbon solvents, ether solvents, ester solvents, aromatic solvents, chlorinated solvents, and the like. In one embodiment, the reaction solvent is removed by distillation and replaced with an ether solvent such as methyl tert-Butyl ether.

The resulting mixture may then be washed with aqueous washes to quench and remove oxidative and acidic components from the mixture. In one embodiment, the mixture may be washed with aqueous sodium thiosulfate (Na$_2$S$_2$O$_3$) to remove oxidative byproducts such as bromine. In another embodiment, the mixture may be washed with a dilute basic aqueous solution to remove acidic components. Suitable bases include alkali metal carbonates and bicarbonates, hydroxides and others. In still another embodiment, the mixture may be further washed with water and brine.

In another embodiment, the reaction mixture may be worked up by filtering the mixture through a suitable filter to remove solid material and the product may be purified by techniques known in the art.

Depending on the scale, the resulting organic solution may be concentrated to provide the solid, which may be purified further by chromatography or recrystallization, or the mixture may be processed to crystallize out the solid directly from solution.

In another embodiment, the reaction mixture is cooled and then concentrated by distilling off a portion of the reaction solvent. The solvent may be replaced by another solvent from which the product will crystallize upon cooling. Once the solvent is switched, the mixture may be heated to dissolve all of the solid and then cooled to crystallize out the product. In one embodiment, the reaction solvent is removed and replaced with isopropanol. In one embodiment, the desired product crystallizes from isopropanol at a suitable concentration when the mixture is cooled to ambient temperature or lower. Transition metal catalyzed coupling reactions of halo-substituted aryl or heteroaryl compounds with various nucleophiles to produce substituted aryl or heteroaryl compounds are also well known in the art (see for example: "Metal-Catalyzed Cross Coupling Reactions", Wiley-VCH publishers, 1998, F. Diedrich and P. J. Stang, chapter 4 by T. N. Mitchell; "Strategic Applications of Named Reactions in Organic Synthesis", Eds. L. Kurti, B. Czako, Elsevier Academic Press, 2005; Suzuki et al., *Tetrahedron Letters* 20 (36): 3437-3440; Corriu, R. J. P. and Masse, J. P., *Journal of the Chemical Society, Chemical Communications* 1972, (3): 144a; Suzuki, A. et al. *Chem. Rev.,* 1995, 95, 2457; Kumada, Makoto et al., *J. Am. Chem. Soc.* 94 (12): 4374-4376; Stille, J. K. et al., *J. Am. Chem. Soc.* 1978, 100, 3636; E-I. Negishi et al., *Journal of the Chemical Society Chemical Communications* 1977, (19): 683; Heck, R. F. et al., J. Org. Chem., 1972, 37 (14): 2320-2322; Heck, R. F., *Acc. Chem. Res.* 1979, 12, 146; Heck, R. F. *Chem. Rev.* 2000, 100, 3009; Sonogashira, K., *J. Organomet. Chem.*, 2002, 653: 46-49; Hartwig, J. F., *Pure Appl. Chem* 1999, 71 (8): 1416-1423; Muci, A. R.; Buchwald, S. L. *Topics in Curr. Chem.* 2002, 219: 131-209; Buchwald et al., *Acc. Chem. Res.,* 1998, 31, 805-818; Hartwig, *Acc. Chem. Res.,* 1998, 31, 852-860). WO 2008/005489 and US 2008/0031902 describes the reaction of a 5-bromo substituted pyrazole compound with tributylvinyl stannane in the presence of tetrakis(triphenylphosphine)palladium to produce the 5-vinyl substituted compound, which is subsequently reduced to form the 5-ethyl substituted compound. Nevertheless, this metal-catalyzed reaction has not been applied to directly in one step introduce alkyl substituents at the 5-position of the pyrazole ring.

In one embodiment, the transition metal catalyst in step (i) of the process is a palladium catalyst. In another embodiment, the metal catalyst is a copper catalyst. In still another embodiment, the metal catalyst is a nickel or rhodium catalyst. In yet another embodiment, the catalyst is a manganese catalyst including, but not limited to, $MnCl_2$.

Palladium catalysts are well known in the art and include Pd(0) and P(II) sources. In one embodiment, palladium on carbon may be used as a catalyst. In another embodiment, a palladium catalyst species may be used which will typically include one or more ligands bound to the palladium metal.

A wide variety of ligands are known in the art, including phosphine ligands, which are typically preferred (see, for example, C. Amatore and A. Jutand, *Coord. Chem. Rev.* 1998, 178-180 and 511-528). Phosphine ligands useful in the process include, but are not limited to, triphenylphosphine, tri(o-tolyl)phosphine (CAS #6163-58-2), tri(2-furyl)phosphine (CAS #5518-52-5), 1,2-bis(diphenylphosphino)ethane (dppe, CAS #1663-45-2), 1,4-bis(diphenylphosphino)butane (dppb), 2,3-bis(diphenylphosphino)butane (Chiraphos), 4,5-Bis(diphenylphosphino)-9,9-dimethylxanthene (Xantphos), 1,2-bis(2,5-dimethylphospholano)benzene (Me-DuPhos), diphenylphosphino)ferrocenyl]ethyldicyclohexylphosphine (Josiphos), bis(diphenylphosphino)methane (dppm, CAS #2071-20-7), 1,4-bis(diphenylphosphino)butane (CAS #7688-25-7), 1,3-bis(diphenylphosphino)propane (dppp, CAS #6737-42-4), 1,2-bis(dicyclohexylphosphino)ethane (dcpe, CAS #23743-26-2), tricyclohexylphosphine (CAS #2622-14-2), tributylphosphine (CAS #998-40-3), tri-tertbutylphosphine (CAS #13716-12-6), tris(pentafluorophenylphosphine) (CAS #1259-35-4), tris(2,4,6-trimethylphenyl)phosphine (CAS #23897-15-6), 2,2'-bis(diphenylphosphino)-1,1'-binaphthyl (binap), (2-biphenyl)di-tertbutylphosphine (CAS #224311-51-7), (2-biphenyl)dicyclohexylphosphine (CAS #247940-06-3), 2-di-tert-butylphosphino-2',4',6'-triisopropylbiphenyl ("tert-Butyl XPhos", CAS #564483-19-8), 2-dicyclohexylphosphino-2',6'-dimethoxybiphenyl ("Sphos", CAS #657408-07-6), 2-dicyclohexylphosphino-2'-(N,N-dimethylamino)biphenyl ("DavePhos", CAS #213697-53-1), 2-dicyclohexylphosphino-2',4',6'-triisopropylbiphenyl ("Xphos", CAS #564483-18-7), and the like.

In addition, the palladium coupling reaction may be performed with N-heterocyclic carbene ligands (see for example, Hillier, A. C. et al., *J. Organomet. Chem.* 2002, 69-82) including, but not limited to, 1,3-Bis(2,4,6-trimethylphenyl)imidazolium chloride (CAS #141556-45-8), 1,3-Bis(2,6-diisopropylphenyl)imidazolium chloride (CAS #250285-32-6), 1,3-Bis(2,6-diisopropylphenyl)imidazolidinium tetrafluoroborate (CAS #282109-83-5), 1,3-bis(2,4,6-trimethylphenyl)imidazolidinium tetrafluoroborate (CAS #141556-45-8), and the like.

The catalyst may be derived from a pre-formed complex, such as $(Ph_3P)_4Pd$, $(Ph_3P)_2PdCl_2$, $(CH_3CN)_2PdCl_2$, $Pd_2(dba)_3$, $(dppf)PdCl_2$ ([1,1'-Bis(diphenylphosphino)ferrocena]palladium(II) dichloride) and the like, or the catalyst may be formed in situ from combinations of palladium sources including, but not limited to, $PdCl_2$, $Pd(OAc)_2$, $Pd(dba)_2$, and the like, and a suitable ligand. In one embodiment, the catalyst is $Pd_2(dba)_3$. In another embodiment, an amine base such as diisopropylethylamine, triethylamine or the like is added to the reaction mixture to stabilize the catalyst.

In another embodiment, the palladium catalyst may be palladium on charcoal. Various types of palladium on charcoal catalysts are commercially available from Johnson-Matthey and other sources.

In another embodiment, the catalyst will be a supported palladium catalyst. These catalysts include the metal, such as palladium, supported on a polymer support that includes metal binding moieties. In one embodiment, the supported polymer is palladium on polymer base fibers including, but not limited to, polyolefin base fibers such as Smopex® polyolefin base fibers from Johnson-Matthey.

In another embodiment, the supported catalyst is a polymer-anchored homogeneous catalyst in which the palladium metal is covalently bound to a polymer chain that may be further linked to an inert polyolefin fiber, which is insoluble in common organic solvents. Suitable supported catalysts include those sold by the trade name FibreCat® from Johnson-Matthey, particularly the 1000 series of FibreCat® supported polymers sold by Johnson-Matthey. Of course, other types of palladium catalysts supported on polymeric supports may be used, including, but not limited to, polystyrene-based supported catalysts and the like.

In some embodiments, it is desirable to remove oxygen from the solvent and/or solution in which the catalyst is present to avoid oxidation of the ligands and destabilization of the catalyst. This may be done in any manner known in the art, such as degassing the mixture by alternately applying a vacuum to the mixture followed by introduction of nitrogen or another suitable inert gas. Alternatively, nitrogen or another inert gas may be bubbled through the solvent or solution containing the catalyst.

In some embodiments of the process when the reaction of step (i) is conducted with the compound of formula (IIc) where M is $BY_2$ or with formula (IId), it may be necessary to add a suitable base to the reaction mixture in addition to a catalyst. Suitable bases include, but are not limited to, alkali metal hydroxides or alkoxides such as NaOH, LiOH and KOH; alkaline earth metal hydroxides or alkoxides, alkali metal carbonates including sodium, potassium, and cesium carbonate, alkaline earth carbonates, alkali metal and alkaline earth phosphates, alkali metal acetates, alkaline earth acetates, and amine bases such as trialkylamines including, but not limited to, triethylamine, diisopropylethylamine, 1,8-Diazabicyclo[5.4.0]undec-7-ene (DBU); 1,5-diazabicyclo[4.3.0]non-3-ene (DBN); 1,4-diazabicyclo[2.2.2]octane (DABCO), and the like.

In one embodiment, step (i) of the process comprises the reaction of a compound of formula (IIB) wherein Q is bromo or iodo. In another embodiment, step (i) of the process comprises the reaction of a compound of formula (IIB) wherein Q is triflate.

In another embodiment, step (i) of the process comprises the reaction of a compound of formula (IIB) wherein Q is bromo, iodo or triflate, with a compound of formula (IIc) wherein M is ZnX RZn or $BY_2$; X is bromo or chloro; R is methyl or ethyl optionally substituted by one or more halogen atoms; and Y is OH or alkoxy.

In another embodiment, step (i) of the process comprises the reaction of a compound of formula (IIB) wherein Q is bromo, iodo or triflate, with a compound of formula (IId) wherein $R^{1d}$, $R^{2d}$, and $R^{3d}$ are independently $C_1$-$C_3$alkyl or $C_1$-$C_3$haloalkyl.

It will be apparent to one of skill in the art that the process of the invention may be adapted to prepare certain arylpyrazole compounds of formula (IB) having certain preferred substitution patterns by selecting appropriate groups for variables $R^{1b}$, $R^{2b}$, $R^{4b}$, $R^{5b}$, $R^{6b}$, $R^{7b}$ and W in the compounds of formulae (IIB), (IIIB) or (IVB).

It will also be appreciated by persons skilled in the art that, within scope of the processes described herein the order of the synthetic steps employed may be varied and will depend inter alia on factors such as the nature of other functional groups present in a particular substrate, the availability of key intermediates, and the protecting group strategy (if any) to be adopted (see e.g. "Protective Groups in Organic Synthesis (Third Edition)", eds. Greene and Wuts, Wiley-Interscience, (1999)). Clearly, such factors will also influence the choice of reagents for use in the said synthetic steps.

The palladium coupling reaction in step (i) is typically conducted in a solvent that does not interfere with the reaction. Useful solvents include, but are not limited to, hydrocarbon solvents, aromatic solvents, ethers, halogenated solvents, ester solvents, ketone solvents, amide solvents, nitrile solvents, and the like. Hydrocarbon solvents include heptane, cyclohexane, methylcyclohexane, isooctane and the like, Aromatic solvents include, but are not limited to, toluene, xylene, ethylbenzene, anisole, and the like. Ethers include, but are not limited to, tetrahydrofuran, 2-methyltetrahydrofuran, ethyl ether, methyl tert-Butyl ether, butyl ether, dioxane, and the like. Ester solvents include alkyl esters such as ethyl acetate, n-propylacetate, isopropyl acetate, n-butylacetate, isobutylacetate, and the like. Nitrile solvents include acetonitrile and the like. Ketone solvents include acetone, methyl ethyl ketone, methyl isobutyl ketone, methyl isopropyl ketone, and others. Amide solvents include dimethylformamide, dimethylacetamide, N-methylpyrrolidone, and the like.

In some embodiments, in step (i) of the process the compound of formula (IIc) will be present in about 0.8 to about 5 molar equivalents based on the amount of compound of formula (IIB). In some embodiments, the amount of the compound of formula (IIc) used in step (i) of the process will be in a molar excess compared with the compound of formula (IIB) so that the best reaction conversion and yield may be obtained. In some embodiments, the compound of formula (IIc) will be present in amount of about 1.0 to about 5 molar equivalents, about 1.0 to about 3 equivalents, about 1.0 to about 2 equivalents or about 1.0 to about 1.5 molar equivalents. In yet another embodiment, the amount of compound of formula (IIc) will be about 1.0 to about 1.3 molar equivalents.

In other embodiments, in step (i) of the process the compound of formula (IId) will be present in about 0.3 to about 5 molar equivalents based on the amount of compound of formula (IIB). In another embodiment, the compound of formula (IId) will be present in about 0.3 to about 2 equivalents. In some embodiments, the amount of the compound of formula (IId) used in step (i) of the process will be slightly in a molar excess compared with the compound of formula (IIB) so that the best reaction conversion and yield may be obtained. In some embodiments, the compound of formula (IId) will be present in amount of about 1.0 to about 2 molar equivalents, about 1.0 to about 1.5 equivalents, about 1.0 to about 1.3 molar equivalents or about 1.0 to about 1.2 molar equivalents.

In yet another embodiment, the amount of the compound of formula (IId) in step (i) will be present in less than 1 molar equivalent based on the compound of formula (IIB), since the compound of formula (IId) contains three methyl groups that may possibly participate in the reaction. In one embodiment, the compound of formula (IId) will be present in about 0.3 to about 1.0 molar equivalents of the compound of formula (IIB). In another embodiment, the compound of formula (IId) will be present in 0.3 to 0.9 equivalents, about 0.5 to about 0.9 equivalents or about 0.7 to about 0.9 molar equivalents of the compound of formula (IIB), In some embodiments, the amount of the catalyst used for step (i) of the process is between about 0.001 to about 0.5 molar equivalents of the pyrazole compound of formula (IIB), between about 0.01 to about 0.5 equivalents, about 0.01 to about 0.25 equivalents, about 0.01 to about 0.15 equivalents or about 0.01 to about 0.1 equivalents. In other embodiments, the amount of catalyst used is about 0.01 to about 0.05, about 0.01 to about 0.025 equivalents or about 0.025 to about 0.075 equivalents. In one embodiment, about 0.05 molar equivalents of the palladium catalyst is used.

In some embodiments where a base is used in the reaction mixture, it may be desired to use an excess of the base. In some embodiments, the amount of the base used is about 0.5 to about 20 molar equivalents of the pyrazole compound of formula (IIB). In other embodiments, the amount of the base is about 1 to about 10 equivalents, about 1 to about 8 equivalents or about 1 to about 5 equivalents. In other embodiments, the amount of the base used is about 2 to about 8 equivalents, about 3 to about 7 equivalents or about 3 to about 5 equivalents.

In another embodiment of the invention, the compound of formula (IB) may be prepared from a 5-amino compound of formula (IIIB) in one step without isolating or purifying any intermediates. In one embodiment, the compound of formula (IIIB) is converted to a diazonium salt that may participate in a coupling reaction with a compound of formula (IIc) or (IId) in the presence of a palladium catalyst. In another embodiment, a compound of formula (IIB) may be formed from the compound of formula (IIIB) and reacted directly with a compound of formula (IIc) or (IId) without isolation.

After the reaction to form the compound of formula (IB) is complete, the reaction mixture may be worked up to remove excess reagents and to purify the desired product from the reaction mixture. Any suitable work-up procedure known in the art may be used to quench and remove excess reagents and to purify and isolate the product.

In one embodiment, the mixture may be added to water or an aqueous solution and mixed to extract undesired components into the aqueous layer. The layers may be separated and the aqueous layer back-extracted with an organic solvent. The combined organic layers may be further washed with brine.

Depending on the scale, the resulting organic solution may be concentrated to provide the solid, which may be purified further by chromatography or recrystallization. In another embodiment, the worked-up mixture may be processed further to crystallize out the solid directly from solution.

In one embodiment, the reaction mixture may be treated with activated carbon to remove impurities and the palladium catalyst. After a suitable period of time mixture may be filtered to remove the activated carbon and impurities. In some embodiments, the filtration may be conducted through a cake of a suitable filter medium such as diatomaceous earth (Celite®) to aid with the removal of the activated carbon and impurities.

In another embodiment, the filtrate is concentrated by distilling off a portion of the solvent. The mixture may be heated to dissolve the solid and then cooled slowly to crystallize the product from solution. In another embodiment, the solvent may be replaced by another solvent from which the product will crystallize upon cooling. Once the product is mixed with the appropriate solvent at a suitable concentration, the mixture may be heated to dissolve all of the solid and then cooled slowly to crystallize out the product. In one embodiment, the desired product crystallizes from isopropanol at a suitable concentration when the mixture is cooled to ambient temperature or lower.

In one embodiment, the process of the invention may be used to prepare compounds of formula (IB) wherein $R^{1b}$ is hydrogen, cyano, halogen, $R^{8b}$, formyl, —$CO_2H$, —C(O)$R^{8b}$, —C(O)O$R^{8b}$, —C(O)N$R^{9b}R^{10b}$ or —C(S)$NH_2$;

$R^{2b}$ is $R^{8b}$ or —S(O)$_m R^{11b}$;

$R^{3b}$ is $C_1$-$C_6$alkyl, $C_1$-$C_6$haloalkyl, $C_1$-$C_6$hydroxyalkyl, $C_3$-$C_8$cycloalkyl, $C_3$-$C_8$halocycloalkyl, $C_2$-$C_6$alkenyl, $C_2$-$C_6$alkynyl, $C_6$-$C_{14}$aryl, $C_5$-$C_{14}$heteroaryl, $C_5$-$C_{14}$heterocyclyl, $R^{8b}$NH, ($R^{8b}$)$_2$N, $R^{8b}$O, $R^{8b}$S or $R^{8b}$C(O)$CH_2$—, wherein each $C_1$-$C_6$alkyl, $C_3$-$C_8$cycloalkyl, $C_2$-$C_6$alkenyl, $C_2$-$C_6$alkynyl, $C_6$-$C_{14}$aryl, $C_5$-$C_{14}$heterocyclyl or $C_5$-$C_{14}$heteroaryl group may optionally be substituted by one or more of halogen, hydroxy, $C_1$-$C_6$alkoxy, $C_1$-$C_6$alkoxy $C_1$-$C_6$alkoxy, amino, $C_1$-$C_6$alkylamino, $C_1$-$C_6$dialkylamino, nitro, cyano or —C(S)$NH_2$;

$R^{4b}$, $R^{5b}$, $R^{7b}$ and $R^{13b}$ are each independently hydrogen, halogen, $C_1$-$C_6$alkyl, $C_1$-$C_6$haloalkyl, cyano or nitro;

$R^{6b}$ is halogen, $C_1$-$C_6$alkyl, $C_1$-$C_6$haloalkyl, $C_1$-$C_6$alkoxy, $C_1$-$C_6$haloalkoxy, cyano, nitro, —C(O)$R^{12b}$, —S(O)$_n R^{12b}$ or $SF_5$;

W is nitrogen or C—$R^{13b}$;

$R^{8b}$ is $C_1$-$C_6$alkyl, $C_1$-$C_6$haloalkyl, $C_1$-$C_6$hydroxyalkyl, $C_3$-$C_8$cycloalkyl, $C_3$-$C_8$halocycloalkyl, $C_2$-$C_6$alkenyl, $C_2$-$C_6$haloalkenyl, $C_2$-$C_6$alkynyl, $C_2$-$C_6$haloalkynyl, $C_6$-$C_{14}$aryl, $C_5$-$C_{14}$heterocyclyl or $C_5$-$C_{14}$heteroaryl;

$R^{9b}$ and $R^{10b}$ are independently hydrogen, $C_1$-$C_6$alkyl, $C_1$-$C_6$haloalkyl, hydroxy or $C_1$-$C_6$alkoxy;

$R^{11b}$ is $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_8$cycloalkyl or $C_3$-$C_8$halocycloalkyl;

$R^{12b}$ is $C_1$-$C_6$alkyl or $C_1$-$C_6$haloalkyl;

m is 0, 1 or 2; and n is 0, 1 or 2.

In another embodiment, the process may be used to prepare compounds of formula (IB) wherein $R^{1b}$ is cyano, —C(O)O$R^{8b}$, —C(O)N$R^{9b}R^{10b}$ or —C(S)$NH_2$;

$R^{2b}$ is —S(O)$_m R^{11b}$;

$R^{3b}$ is $C_1$-$C_3$alkyl or $C_1$-$C_3$haloalkyl;

$R^{4b}$, $R^{5b}$, $R^{7b}$ and $R^{13b}$ are each independently hydrogen or halogen;

$R^{6b}$ is $C_1$-$C_6$haloalkyl, $C_1$-$C_6$haloalkoxy or $SF_5$;

W is C—$R^{13b}$;

$R^{8b}$ is $C_1$-$C_6$alkyl or $C_1$-$C_6$haloalkyl;

$R^{9b}$ and $R^{10b}$ are independently hydrogen, $C_1$-$C_6$alkyl or $C_1$-$C_6$haloalkyl;

$R^{11b}$ is $C_1$-$C_3$haloalkyl;

$R^{12b}$ is $C_1$-$C_6$alkyl or $C_1$-$C_6$haloalkyl;

m is 0, 1 or 2; and n is 0, 1 or 2.

In yet another embodiment of the invention, the process may be used to prepare compounds of formula (IB) wherein $R^{1b}$ is cyano or —C(S)$NH_2$;

$R^{2b}$ is —S(O)$_m R^{11b}$;

$R^{3b}$ is methyl or ethyl, optionally substituted with one to five halogen atoms;

$R^{4b}$, $R^{5b}$, $R^{7b}$ and $R^{13b}$ are each independently hydrogen or halogen;

$R^{6b}$ is $C_1$-$C_6$haloalkyl;

W is C—$R^{13b}$;

$R^{11b}$ is $CF_3$, $CClF_2$ or $CCl_2F$;

m is 0, 1 or 2; and n is 0, 1 or 2.

In one embodiment of the second aspect of the invention, the process of the invention may be used to prepare compounds of formula (IB) wherein $R^{1b}$ is cyano, —C(O)$R^{8b}$, —C(O)O$R^{8b}$, —C(O)N$R^{9b}R^{10b}$ or —C(S)$NH_2$.

In another embodiment of the second aspect of the invention, the process of the invention may be used to prepare compounds of formula (IB) wherein $R^{3b}$ is $C_1$-$C_6$ alkyl, optionally substituted by one or more halogen atoms.

In yet another embodiment of the second aspect of the invention, the process of the invention may be used to prepare compounds of formula (IB) wherein $R^{3b}$ is methyl or ethyl optionally substituted with one to five halogen atoms.

In one embodiment of the second aspect of the invention, the process of the invention may be used to prepare compounds of formula (IB) where $R^{2b}$ is —S(O)$_m R^{11b}$ where $R^{11b}$ is $C_1$-$C_3$ alkyl or $C_1$-$C_3$ haloalkyl.

In one embodiment of the second aspect of the invention, the process of the invention may be used to prepare compounds of formula (IB) wherein $R^{3b}$ is methyl, —$CH_2F$, —$CHF_2$, $CF_3$, ethyl, —$CHFCH_3$, —$CF_2CH_3$, —$CF_2CF_3$, or —$CHFCF_3$; W is $CR^{13b}$; $R^{4b}$ and $R^{13b}$ are halogen; $R^{5b}$ and $R^{7b}$ are hydrogen; and $R^{6b}$ is $CF_3$.

In one embodiment of the second aspect of the invention, the process of the invention may be used to prepare compounds of formula (IB) where $R^{2b}$ is —S(O)$_m R^{11b}$ where $R^{11b}$ is methyl, ethyl, —$CF_3$, —$CCl_2F$ or —$CF_2Cl$.

In one embodiment of the second aspect of the invention, the process of the invention may be used to prepare compounds of formula (IB) wherein $R^{1b}$ is cyano, —C(O)$R^{8b}$, —C(O)O$R^{8b}$, —C(O)N$R^9R^{10}$ or —C(S)$NH_2$; and $R^{3b}$ is $C_1$-$C_6$ alkyl, optionally substituted by one or more halogen atoms.

In one embodiment of the second aspect of the invention, the process of the invention may be used to prepare compounds of formula (IB) wherein $R^{1b}$ is cyano, —C(O)OR$^8$ or —C(O)NR$^9$R$^{10}$; and $R^3$ is methyl or ethyl optionally substituted by one to five halogen atoms.

In another embodiment of the second aspect of the invention, the process of the invention may be used to prepare compounds of formula (IB) wherein $R^{1b}$ is cyano; $R^3$ is methyl or ethyl optionally substituted by one to five halogen atoms; and $R^{2b}$ is —S(O)$_m$R$^{11b}$ where $R^{11b}$ is $C_1$-$C_3$ alkyl or $C_1$-$C_3$ haloalkyl.

In one embodiment of the second aspect of the invention, the process of the invention may be used to prepare compounds of formula (IB) wherein $R^{1b}$ is cyano; $R^{3b}$ is methyl, —CH$_2$F, —CHF$_2$, CF$_3$, ethyl, —CHFCH$_3$, —CF$_2$CH$_3$, —CF$_2$CF$_3$, or —CHFCF$_3$; and $R^{2b}$ is —S(O)$_m$R$^{11b}$ where $R^{11b}$ is methyl, ethyl, —CF$_3$, —CCl$_2$F or —CF$_2$Cl.

In one preferred embodiment of the second aspect of the invention, the process of the invention may be used to prepare compounds of formula (IB) wherein $R^{1b}$ is cyano; $R^{3b}$ is methyl or ethyl; and $R^{2b}$ is —S(O)$_m$R$^{11b}$ where $R^{11b}$ is CF$_3$, —CCl$_2$F or —CF$_2$Cl.

It will be apparent to those of skill in the art, that certain compounds of formulae (I) and (IB) may be prepared by further elaborating the functional groups present in the compounds, for example, by converting an ester —C(O)OR$^{8b}$ at the 3- or 5-position of the pyrazole ring to a carboxylic acid, a hydroxymethyl group, an amide and the like using well known functional group transformations. Furthermore, as described in U.S. Pat. No. 7,759,381, an ester group may be converted to a cyano group by hydrolysis to the carboxylic acid, formation of an amide and treatment of the amide with a dehydrating agent such as SOCl$_2$. The group —C(S)NH$_2$ may be formed from the corresponding cyano group by treatment with hydrogen sulfide, as described in U.S. Pat. Nos. 6,265,430 and 6,518,296, both incorporated herein by reference in their entirety.

In another embodiment of the invention, compounds of formulae (I) and (IB) wherein $R^3$ and $R^{3b}$ are halomethyl are formed by reaction of the corresponding compounds of formulae (I) and (IB) in which $R^3$ and $R^{3b}$, respectively, are hydroxymethyl with halogenating reagents, including brominating reagents such as a mixture of bromine or N-bromosuccinimide and triphenylphosphine, hydrobromic acid; or fluorinating reagents such as dimethylaminosulfur trifluoride, diethylaminosulfur trifluoride (DAST™) or bis(2-methoxyethyl)aminosulfur trifluoride (Deoxofluor™). The reaction is usually performed in a solvent such as methylene chloride, chloroform and generally at temperatures between −100° C. and 40° C. A summary of such methods is found in Comprehensive Organic Transformations, VCH Publishers, 1989, R. C. Larock, pp. 353-360.

Functional group modification steps to modify the functional groups in the compounds of formulae (I) and (IB) include, but are not limited to:
(a) hydrolysis of an ester or amide to a carboxylic acid —CO$_2$H;
(b) a decarboxylation step;
(c) coupling of the carboxylic acid with an amine to form an amide;
(d) conversion of a carboxylic acid to an acyl halide;
(e) (i) reduction of the —CO$_2$H moiety to —CH$_2$OH;
(ii) an oxidation step to form —CHO;
(iii) reaction of a formyl group, an ester group or an amide group with an alkyl or aryl metal nucleophile such as a Grignard reagent (e.g. R$^8$—Mg-halogen or R$^{8b}$—Mg-halogen) or an organolithium reagent (e.g. R$^8$—Li or R$^{8b}$—Mg-halogen, where R$^8$ and R$^{8b}$ are as defined above for formula (I) or (IB));
(iv) an additional oxidation step; or
(ia) reacting the —CO$_2$H moiety with an agent to form the corresponding N-methoxy-N-methyl amide (Weinreb amide); and
(iia) reaction with an alkyl or aryl metal nucleophile such as a Grignard reagent (e.g. R$^8$—Mg-halogen or R$^{8b}$—Mg-halogen, where R$^8$ and R$^{8b}$ are as defined above for formula (I) or (IB)) or an organolithium reagent (e.g. R$^8$—Li or R$^{8b}$—Li, where R$^8$ and R$^{8b}$ are as defined above for formula (I) or (IB)).

General ketone formation from Weinreb amides is described in *March's Advanced Organic Chemistry*—Reactions, Mechanisms and Structure (6$^{th}$ Edition), ed. Michael B. Smith and Jerry March, Wiley Interscience (John Wiley & Sons, Inc.), page 1448, (2007).

In one embodiment, a decarboxylation of a compound of formulae (I) or (IB) having a carboxyl group —CO$_2$H on the 3- and/or 5-position of the pyrazole ring provides a compound wherein the corresponding position is hydrogen.

In another embodiment of the invention, a decarboxylation step followed by a halogenation step provides a compound of formulae (I) or (IB) wherein the corresponding position on the pyrazole ring is a halogen atom. An example of a general process for decarboxylation followed by halogenations is Morimoto et al, "Synthesis of Halosulfuron-methyl via Selective Chlorination at 3- and/or 5-position of Pyrazole-4-carboxylates", *J. Het. Chem.*, 34: 537-540 (1997).

In another embodiment of the invention, a compound of formula (I) or (IB) having a carboxylic acid substituent is reacted with an amine HNR$^9$R$^{10}$ or HNR$^{9b}$R$^{10b}$, where R$^9$, R$^{10}$, R$^{9b}$ and R$^{10b}$ are as defined above for formulae (I) and (IB), in presence of coupling agents such as dicyclohexylcarbodiimide and the like, to form a compound of formula (I) where R$^1$ and/or R$^3$ is CONR$^9$R$^{10}$; or a compound of formula (IB) where R$^{1b}$ and/or R$^{3b}$ is CONR$^{9b}$R$^{10b}$. A general description of this transformation is described in *March's Advanced Organic Chemistry*—Reactions, Mechanisms and Structure (6$^{th}$ Edition), ed. Michael B. Smith and Jerry March, Wiley Interscience (John Wiley & Sons, Inc.), page 1430-1434 (16-74—Acylation of Amines by Carboxylic Acids—Amino-dehydroxylation), (2007).

In another embodiment of the invention, the functional group modification comprises reacting a compound of formula (I) where R$^1$ and/or R$^3$ is C(O)NH$_2$ or a compound of formula (IB) where R$^{1b}$ is C(O)NH$_2$ with a dehydrating agent such as thionyl chloride, oxalyl chloride and the like, to form the compound of formula (I) where R$^1$ and/or R$^3$ is cyano or a compound of formula (IB) wherein R$^{1b}$ is cyano. A general description of this transformation is described in *March's Advanced Organic Chemistry*—Reactions, Mechanisms and Structure (6$^{th}$ Edition), ed. Michael B. Smith and Jerry March, Wiley Interscience (John Wiley & Sons, Inc.), page 1549-1550 (17-30—Dehydration of Unsubstituted Amides—N,N-dihydro-C-oxo-bielimination), (2007).

In another embodiment of the invention, the process further comprises reacting a compound of formula (I) where R$^1$ and/or R$^3$ is an amide C(O)NH$_2$ or a compound of formula (IB) where R$^{1b}$ is —C(O)NH$_2$ with 2,4-bis(4-methoxyphenyl)-1,3,2,4-dithiadiphosphetane-2,4-disulfide (known as Lawesson's reagent) and related reagents to form the thioamide of formula (I) wherein R$^1$ and/or R$^3$ is C(S)NH$_2$ or a compound of formula (IB) where R$^{1b}$ is C(S)NH$_2$. A general description of this transformation is described in *March's Advanced Organic Chemistry*—Reactions, Mechanisms and Structure (6$^{th}$ Edition), ed. Michael B. Smith and Jerry March, Wiley Interscience (John Wiley & Sons, Inc.), page 1277-1278 (16-11—The Addition of $H_2S$ and Thiols to Carbonyl Compounds—O-Hydro-C-mercapto-addition), (2007).

In another embodiment of the invention, the process comprises: (i) reduction of a —$CO_2H$ moiety on the pyrazole ring to —$CH_2OH$; (ii) oxidation of the —$CH_2OH$ moiety to form a —CHO moiety; (iii) reaction of the —CHO moiety with a Grignard reagent (e.g. $R^8$—Mg-halogen or $R^{8b}$—Mg-halogen) or an organolithium reagent ($R^8$—Li or $R^{8b}$—Li); and (iv) an additional oxidation step.

In another embodiment of the invention, the process further comprises: (i) reduction of a —$CO_2H$ moiety on the pyrazole ring to —$CH_2OH$; (ii) oxidation of the —$CH_2OH$ moiety to form a —CHO moiety in the compound of formula (IIa); (iii) reaction with a Grignard reagent (e.g. $R^8$—Mg-halogen or $R^{8b}$—Mg-halogen) or an organolithium reagent (e.g. $R^8$—Li or $R^{8b}$—Li); and (iv) additional reduction steps of the resulting hydroxyl moiety to yield the compound of formula (I) wherein $R^1$ and/or $R^3$ is $R^8$ or a compound of formula (IB) where $R^{1b}$ is $R^{8b}$.

In one preferred embodiment of the invention, where $R^1$ in the compound of formula (I) is —$C(O)OR^8$ or $R^{1b}$ in the compound of formula (IB) is —$C(O)OR^8$, the compound is further derivatized to convert the ester group to a CN group via a four step process wherein step one comprises hydrolyzing the ester group to form a carboxylic acid, step two comprises reacting the carboxylic acid with a halogenating agent to form a acyl halide, step three comprises reacting the acyl halide with ammonia to form an unsubstituted amide group —$C(O)NH_2$, and step four comprises reacting the compound bearing the unsubstituted amide group with a dehydrating agent such as $SOCl_2$ to form the compound of formula (I) or (IB) substituted with a cyano group at the 3-position of the pyrazole ring. This process is described in U.S. Pat. No. 7,759,381 B2 to Lee et al., incorporated herein by reference, and illustrated for the compound of formula (I) in the scheme below:

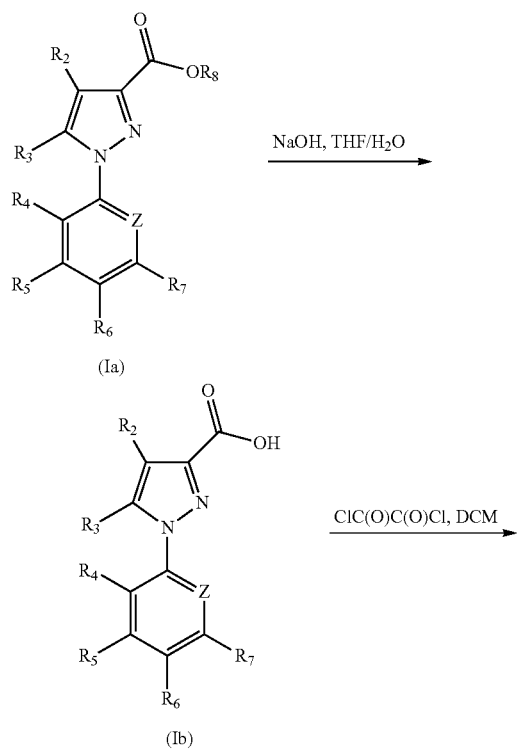

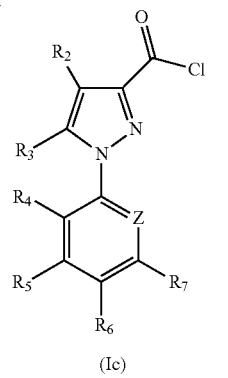

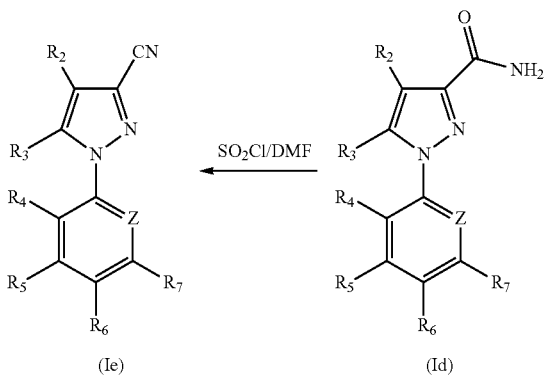

The acids, bases and solvents and the individual process steps such as alkylation, Grignard reaction/reagents, halogenation and oxidation used in the invention will be apparent to those of ordinary skill in the art (e.g. *Vogel's Textbook of Practical Organic Chemistry* (Fifth Edition), Furniss et al., Longman Scientific & Technical (1989); *Protective Groups in Organic Synthesis* (Third Edition), Greene & Wuts, Wiley Interscience (1999); *March's Advanced Organic Chemistry: Reactions, Mechanisms, and Structure* (6th Edition), March & Smith, Wiley, (2007); *Advanced Organic Chemistry (Part A—Structure and Mechanisms—4th Edition)*, Carey & Sundberg, Springer Science (2000); *Advanced Organic Chemistry (Part B—Reaction and Synthesis—4th Edition)*, Carey & Sundberg, Springer Science (2001); *Strategic Applications of Named Reactions in Organic Synthesis*, Kurti and Czako, Academic Press (2005).

The invention is further described by the following non-limiting examples which further illustrate the invention, and are not intended, nor should they be interpreted to, limit the scope of the invention.

EXAMPLES

All temperatures are given in degrees Centigrade; room temperature means 20 to 25° C. Reagents were purchased from commercial sources or prepared following literature procedures.

Unless otherwise noted, purification by column chromatography was performed by dissolving the crude residue in a small volume of an appropriate solvent, preferably a solvent used in the purification, and eluting the mixture through a column packed with silica gel. In some cases, the compounds were purified by HPLC purification system managed by the Chromeleon™ software using a 50 mm Varian Dynamax HPLC 21.4 mm Microsorb Guard-8 C8 column. The resulting fractions were analyzed, combined as appropriate, and then evaporated to provide purified material.

Proton and fluorine magnetic resonance (respectively 1H NMR and 19F NMR) spectra were recorded on a Varian INOVA NMR spectrometer [400 MHz (1H) and 377 MHz (19F)]. All spectra were determined in the solvents indicated. Chemical shifts are reported in ppm downfield of tetramethylsilane (TMS), referenced to the residual proton peak of the respective solvent peak for 1H NMR. Interproton coupling constants are reported in Hertz (Hz). LC-MS spectra were obtained using a Thermofinnigan AQA MS ESI instrument, using a Phenomenex Aqua 5 micron C18 125A 50×4.60 mm column and a linear gradient from 55% MeOH: 1% CH$_3$CN in H2O to 100% MeOH over 3 minutes. 100% MeOH was maintained for 2 minutes. Melting points were determined using a Thomas Hoover capillary melting point apparatus and are uncorrected.

Example 1

Preparation of 1-(2-Chloro-6-fluoro-4-trifluoromethyl-phenyl)-5-methyl-4-trifluoromethanesulfinyl-1H-pyrazole-3-carbonitrile (Compound 1)

Compound 1 was prepared using a process according to the first aspect of the invention as depicted in Scheme 1 and described below.

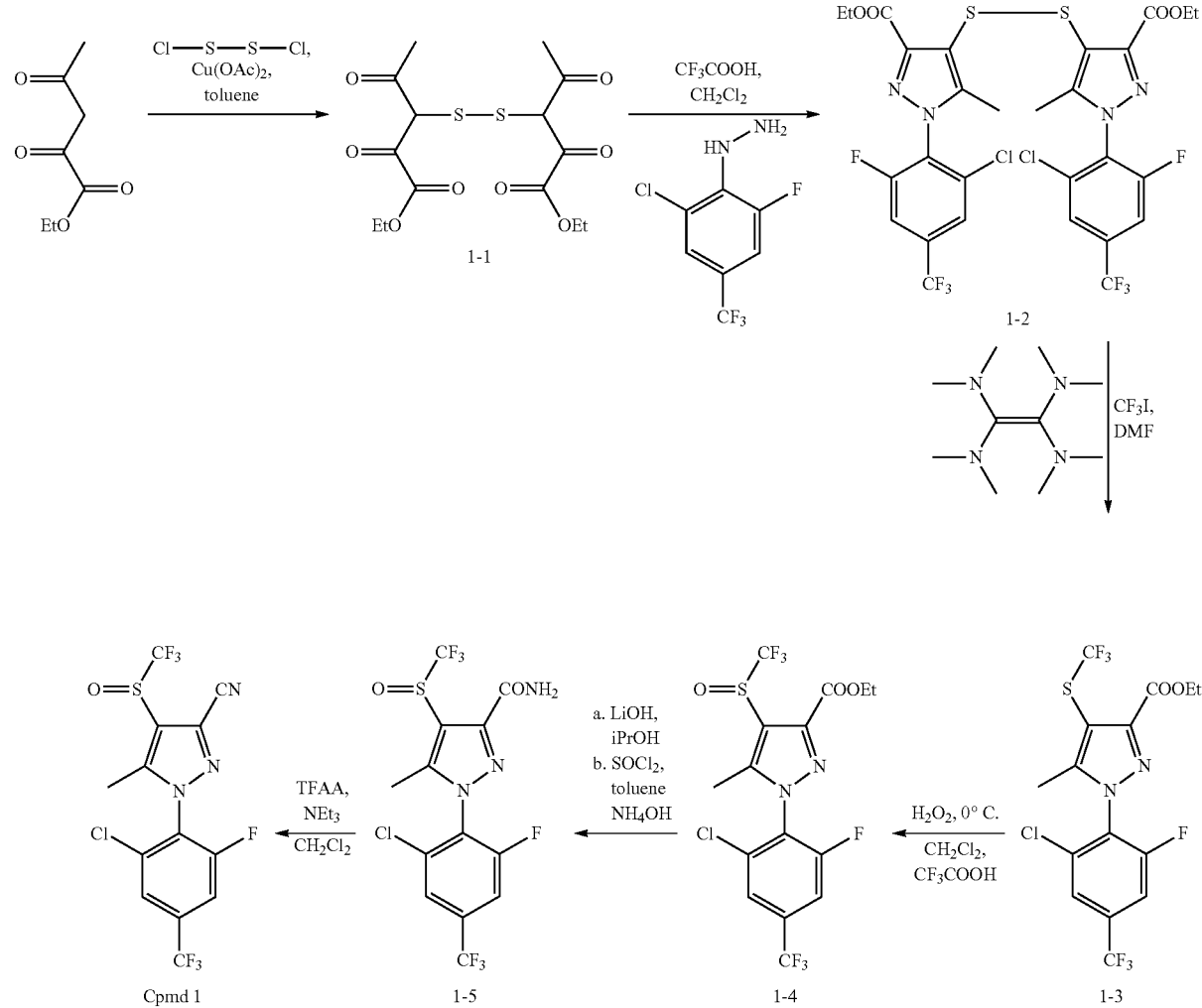

3-(1-Ethoxyoxalyl-2-oxo-propyldisulfanyl)-2,4-dioxo-pentanoic acid ethyl ester (1-1)

To a well stirred solution of ethyl dioxovalerate (20 g, 126 mmol) in toluene (300 mL) was added copper (II) acetate (27.5 g, 151 mmol) at 7° C. and the resulting mixture was stirred at 7° C. for 1.5 h then cooled to 0° C. Sulfur monochloride (9.4 g, 70 mmol) was added to the mixture slowly at 0° C. and the reaction mixture was stirred at 0° C. for additional 2.5 h. Aqueous hydrochloric acid (1 N, 350 mL) was added to reaction mixture and the resulting mixture was stirred at room temperature for 16 h. The reaction mixture was filtered, the layers of the filtrate were separated and the aqueous layer was extracted with toluene. The combined organic layers were concentrated under reduced pressure. The residue was diluted with ethanol (110 mL). The resulting precipitate was collected by suction filtration and washed with ethanol to afford 3-(1-Ethoxyoxalyl-2-oxo-propyldisulfanyl)-2,4-dioxo-pentanoic acid ethyl ester as a green solid (13.5 g, 36 mmol, 56%) $^1$H NMR (400 MHz, CDCl$_3$) δ ppm 1.37 (t, J=7.1 Hz, 6H), 2.46 (s, 6H), 3.74 (m, 2H), 4.33 (q, J=7.1 Hz, 4H).

Phenylpyrazole Disulfide (1-2)

To a solution of 2-Chloro-6-fluoro-4-(trifluoromethyl) phenylhydrazine (7.3 g, 42 mmol) in dichloromethane (50 mL) was added trifluoroacetic acid (18.6 g, 160 mmol) at 0° C. The reaction mixture was stirred at 0° C. for 1 h and 3-(1-Ethoxyoxalyl-2-oxo-propyldisulfanyl)-2,4-dioxo-pentanoic acid ethyl ester (7.2 g, 19 mmol) was added. The reaction mixture was stirred at 0° C. for 1 h before it was allowed to warm to room temperature slowly. Volatiles were evaporated under reduced pressure. The residue was purified by column chromatography, elution with heptanes/EtOAc, to give the desired product (2) as pale yellow solid (7.5 g, 11 mmol, 62%). $^1$H NMR (400 MHz, CDCl$_3$) δ ppm 1.39-1.43 (m, 6H), 2.06 (s, 3H), 2.08 (s, 3H), 4.37-4.50 (m, 4H), 7.47 (dd, J=8.2, 1.4 Hz, 2H), 7.67 (s, 2H). 19F NMR (376 MHz, CDCl$_3$) δ ppm −113.8 (d, J=7.9 Hz, 1F), −113.5 (d, J=8.6 Hz, 1F), −63.7 (s, 3F), −63.7 (s, 3F).

1-(2-Chloro-6-fluoro-4-trifluoromethyl-phenyl)-5-methyl-4-trifluoromethylsulfanyl-1H-pyrazole-3-carboxylic acid ethyl ester (1-3)

To a well stirred solution of disulfide 2 (3.9 g, 5.9 mmol) in DMF (20 mL) was added tetradimethylaminoethylene (2.1 g, 10.5 mmol) at −60° C., followed by iodotrifluoromethane (5.0 g, 25.5 mmol). The reaction mixture was slowly warmed to −5° C. The reaction flask was transferred to an ice bath and was stirred at 0° C. for an additional 1 h. The reaction was quenched with ether and water. The reaction mixture was diluted with ether and the layers were separated. The organic layer was dried (MgSO$_4$) and concentrated under reduced pressure. The residue was purified by column chromatography, elution with heptanes/EtOAc, to provide 1-(2-Chloro-6-fluoro-4-trifluoromethyl-phenyl)-5-methyl-4-trifluoromethylsulfanyl-1H-pyrazole-3-carboxylic acid ethyl ester as off white solid (3.6 g, 8.0 mmol, 77%). $^1$H NMR (400 MHz, CDCl$_3$) δ ppm 1.43 (t, J=7.1 Hz, 3H), 2.31 (s, 3H), 4.47 (q, J=7.1 Hz, 2H), 7.52 (dd, J=8.3, 1.5 Hz, 1H), 7.69 (s, 1H). $^{19}$F NMR (376 MHz, CDCl$_3$) δ ppm −113.3 (d, J=7.9 Hz, 1F), −63.8 (s, 3F), −44.4 (s, 3F)

1-(2-Chloro-6-fluoro-4-trifluoromethyl-phenyl)-5-methyl-4-trifluoromethanesulfinyl-1H-pyrazole-3-carboxylic acid ethyl ester (1-4)

To a solution of 1-(2-Chloro-6-fluoro-4-trifluoromethyl-phenyl)-5-methyl-4-trifluoromethylsulfanyl-1H-pyrazole-3-carboxylic acid ethyl ester (1.2 g, 2.7 mmol) in dichloromethane (6 mL) was added trifluoroacetic acid (2.4 mL) at 0° C. To the reaction mixture was added an aqueous solution of hydrogen peroxide (30 wt %, 0.9 g, 8.3 mmol) at 0° C. The reaction mixture was stirred at 0° C. for 6 h. The reaction was quenched by addition of a solution of sodium bisulfite (0.8 g) in water (12 mL). The resulting mixture was extracted with dichloromethane. The organic layer was dried (Na$_2$SO$_4$) and concentrated under reduced pressure. The residue was purified by column chromatography, elution with heptanes/ EtOAc, to give 1-(2-Chloro-6-fluoro-4-trifluoromethyl-phenyl)-5-methyl-4-trifluoromethanesulfinyl-1H-pyrazole-3-carboxylic acid ethyl ester as a white solid (1.2 g, 2.6 mmol, 99%). $^1$H NMR (400 MHz, CDCl$_3$) δ ppm 1.42 (t, J=7.1 Hz, 3H), 2.51 (s, 3H), 4.36-4.55 (m, 2H), 7.54 (dd, J=8.3, 1.6 Hz, 1H), 7.72 (s, 1H). $^{19}$F NMR (376 MHz, CDCl$_3$) δ ppm −113.2 (d, J=7.9 Hz, 0.5F), −112.8 (d, J=9.2 Hz, 0.5F), −74.0 (s, 1.5F), −73.8 (s, 1.5F), −63.8 (s, 3F).

1-(2-Chloro-6-fluoro-4-trifluoromethyl-phenyl)-5-methyl-4-trifluoromethanesulfinyl-1H-pyrazole-3-carboxylic acid amide (1-5)

a. 1-(2-Chloro-6-fluoro-4-trifluoromethyl-phenyl)-5-methyl-4-trifluoromethanesulfinyl-1H-pyrazole-3-carboxylic acid To a solution of 1-(2-Chloro-6-fluoro-4-trifluoromethyl-phenyl)-5-methyl-4-trifluoromethanesulfinyl-1H-pyrazole-3-carboxylic acid ethyl ester (1.2 g, 2.6 mmol) in isopropanol (10 mL) and water (2.5 mL) was added lithium hydroxide (0.2 g, 8.4 mmol) at 0° C. The reaction mixture was stirred at 0° C. for 2 h. To the reaction mixture was added aqueous hydrochloric acid (37 wt %, 0.9 mL) and water (7 mL). The resulting mixture was extracted with EtOAc. The organic layer was washed with water, dried (MgSO$_4$) and concentrated under reduced pressure to give 1-(2-Chloro-6-fluoro-4-trifluoromethyl-phenyl)-5-methyl-4-trifluoromethanesulfinyl-1H-pyrazole-3-carboxylic acid as an off-white solid (1.1 g). This material was used without purification for the next step. $^1$H NMR (400 MHz, CDCl$_3$) δ ppm 2.52 (s, 3H), 7.56 (dd, J=8.3, 1.5 Hz, 1H), 7.73 (s, 1H). $^{19}$F NMR (376 MHz, CDCl$_3$) δ ppm −113.4 (d, J=8.6 Hz, 0.5F), −112.9 (d, J=7.9 Hz, 0.5F), −73.9 (s, 1.5F), −73.7 (s, 1.5F), −63.8 (s, 3F).

b. 1-(2-Chloro-6-fluoro-4-trifluoromethyl-phenyl)-5-methyl-4-trifluoromethanesulfinyl-1H-pyrazole-3-carboxylic acid amide (1-5)

To a solution of 1-(2-Chloro-6-fluoro-4-trifluoromethyl-phenyl)-5-methyl-4-rifluoromethanesulfinyl-1H-pyrazole-3-carboxylic acid (1.07 g) in toluene (5.4 mL) was added DMF (0.03 mL) and then thionyl chloride (0.49 g, 4.1 mmol) at room temperature. The reaction mixture was heated at 60° C. for 2 h. After the reaction mixture was cooled to room temperature, it was added drop-wise to aqueous ammonium hydroxide (20%, 3.5 mL) at 0° C. The resulting mixture was extracted with EtOAc after it was diluted with water. The organic layer was dried over (MgSO4) and concentrated under reduced pressure to afford 1-(2-Chloro-6-fluoro-4-trifluoromethyl-phenyl)-5-methyl-4-trifluoromethanesulfinyl-1H-pyrazole-3-carboxylic acid amide as an off white solid (1.17 g). This material was used without purification for the next step $^1$H NMR (400 MHz, CDCl$_3$) δ ppm 2.49 (s, 3H), 5.89 (br. s., 1H), 6.72 (br. s., 1H), 7.57 (dd, J=8.3, 1.4 Hz, 1H), 7.74 (s, 1H). $^{19}$F NMR (376 MHz, CDCl$_3$) δ ppm −113.4 (d, J=7.9 Hz, 0.5F), −113.1 (d, J=8.6 Hz, 0.5F), −74.0 (s, 1.5F), −73.8 (s, 1.5F), −63.8 (d, J=1.3 Hz, 3F)

1-(2-Chloro-6-fluoro-4-trifluoromethyl-phenyl)-5-methyl-4-trifluoromethanesulfinyl-1H-pyrazole-3-carbonitrile (Compound 1)

To a solution of 1-(2-Chloro-6-fluoro-4-trifluoromethyl-phenyl)-5-methyl-4-trifluoromethanesulfinyl-1H-pyrazole-3-carboxylic acid amide (0.98 g) in dichloromethane (5 mL) was added triethylamine (0.63 g, 6.2 mmol) followed by trifluoroacetic anhydride (0.89 g, 4.2 mmol) at 0° C. The reaction mixture was stirred at 0° C. for 3 h and quenched by addition of water (2.0 mL) at 0° C. The resulting mixture was extracted with dichloromethane after it was warmed to room temperature. The organic layer was dried (Na$_2$SO$_4$) and concentrated under reduced pressure. The residue was purified by column chromatography, elution with heptanes/EtOAc, to provide 1-(2-Chloro-6-fluoro-4-trifluoromethyl-phenyl)-5-methyl-4-trifluoromethanesulfinyl-1H-pyrazole-3-carbonitrile as a white solid (0.85 g, 2.0 mmol, 99% in three steps). $^1$H NMR (400 MHz, CDCl$_3$) δ ppm 2.45 (s, 3H), 7.55-7.63 (m, 1H), 7.76 (s, 1H). $^{19}$F NMR (376 MHz, CDCl$_3$) δ ppm −113.3 (d, J=7.9 Hz, 0.5F), −113.0 (d, J=7.9 Hz, 0.5F), −73.9 (s, 1.5F), −73.8 (s, 1.5F), −63.9 (s, 3F).

Example 2

Preparation of 1-(2-Chloro-6-fluoro-4-trifluoromethyl-phenyl)-5-methyl-4-trifluoromethanesulfinyl-1H-pyrazole-3-carbonitrile (Compound 1) according to the second aspect of the invention Compound 1 was prepared using a process according to the second aspect of the invention as depicted in Scheme 2 and described below. As shown in Scheme 2, Compound 1, which has a mixed chloro-fluoro substitution on the phenyl ring, was synthesized in six steps starting from carboxylic acid 2-1. However, it will be appreciated by one of skill in the art that the process may begin with any readily-available 5-aminophenylpyrazole compound of formula (IIIB) such as fipronil, a 5-halo-1-arylpyrazole or 5-haloalkylsulfonate compound of formula (IIB) or other suitable phenylpyrazole compounds.

The carboxylic acid 2-1 was converted into aniline 2-2 via Curtius rearrangement. Then chlorination of 2-2 with NCS gave aniline 2-3. Cyclo-condensation of aniline 2-3 with ethyl 2,3-dicyanopropanoate then decarboxylation afforded pyrazole 2-4. Sulfinylation of pyrazole 2-4 with CF$_3$SOCl gave 2-5. Conversation the amino group of 2-5 to bromine afforded 2-6. Palladium-coupled cross-coupling of 2-6 with Me$_2$Zn provided the desired methylated product Compound 1.

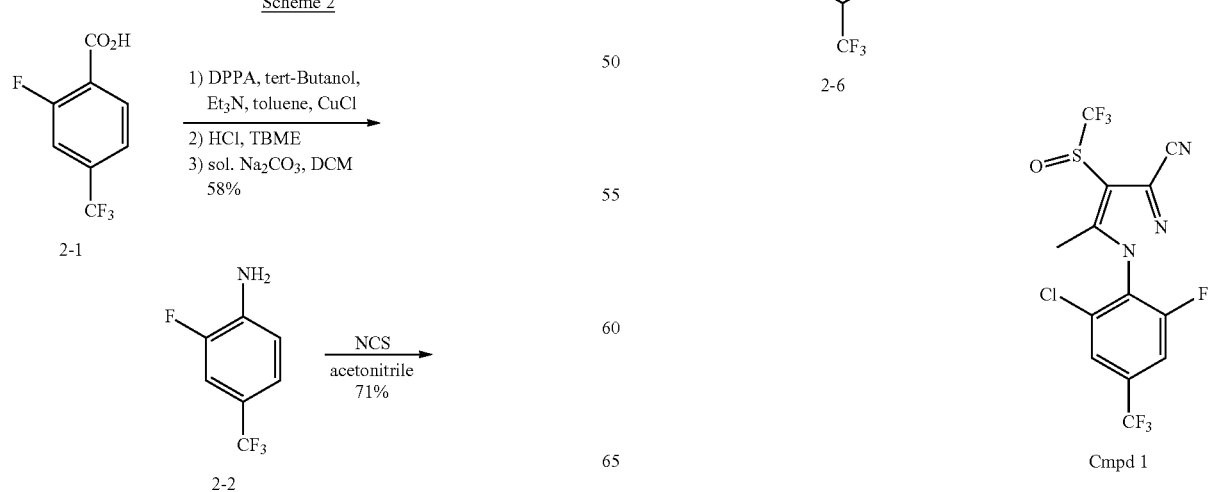

Step 1 Synthesis of 2-fluoro-4-(trifluoromethyl)aniline

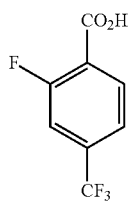 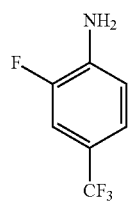

1) DPPA, tert-Butanol, Et$_3$N, toluene, CuCl
2) HCl, TBME
3) sol. Na$_2$CO$_3$, DCM To the solution of 2-fluoro-4-(trifluoromethyl)benzoic acid (1 kg, 4.805 mol, 1.00 equivalent "eq.") and CuCl (14.26 g, 0.144 mol, 0.03 eq.) in t-BuOH (11.7 L) was added triethylamine (TEA, 533.8 g, 5.286 mol, 1.10 eq.) dropwise at room temperature (rt). Then the solution was heated to 50° C. and diphenylphosphoryl azide (DPPA, 1393 g, 5.045 mol, 1.05 eq.) was added dropwise to the solution at 50-60° C. After heating at 80~85° C. overnight the solution was concentrated under vacuum. The residual was dissolved in H$_2$O and filtered. The filtrate was extracted with ethyl acetate. The organic layers was dried with Na$_2$SO$_4$, filtered and concentrated under vacuum. The residual was dissolved in tert-Butyl methyl ether (TBME) and HCl (gas) was bubbled in for 2 hours. The filtrate was collected and dissolved in water and basified with 2 M NaOH. The solution was extracted with TBME. The organic layers were dried and concentrated under vacuum to give 2-fluoro-4-(trifluoromethyl) aniline (498 g, 58%) as a red oil.

$^1$H-NMR (300 MHz, CDCl$_3$) δ 7.27 (m, 2H), 6.82 (m, 1H), 4.05 (bs, 2H)

MS: m/z=180 [M+H]$^+$

Step 2 Synthesis of 2-chloro-6-fluoro-4-(trifluoromethyl)aniline

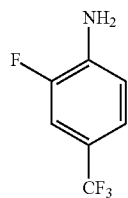 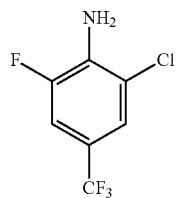

NCS, acetonitrile

To a solution of 2-fluoro-4-(trifluoromethyl)aniline (498 g, 2.783 mmol, 1.00 eq.) in acetonitrile (5 L) was added N-chlorosuccinimide (NCS, 408 g, 3.06 mmol, 1.1 eq.). Then the solution was heated under reflux for 3 hours and then concentrated under vacuum, diluted with petroleum ether (PE 1 L) and filtered. The filtrate was concentrated under vacuum to afford a red oil. The oily product was purified by vacuum distillation to give 2-chloro-6-fluoro-4-(trifluoromethyl) aniline as a yellow liquid (420 g, 71%).

$^1$H-NMR (300 MHz, CDCl$_3$) δ 7.37 (s, 1H), 7.20 (dd, J=10.5 Hz, J=1.5 Hz, 1H), 4.43 (bs, 2H)

$^{19}$F NMR (282 MHz, CDCl3): −63.24 (s, 3F), −111.04 (s, 1F)

MS: m/z=214 [M+H]$^+$

Step 3 Synthesis of 5-amino-1-(2-chloro-6-fluoro-4-(trifluoromethyl)phenyl)-1H-pyrazole-3-carbonitrile

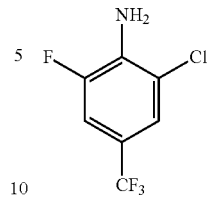

1) NaNO$_2$, H$_2$SO$_4$, AcOH
2) NaOAc, H$_2$O, ethyl 2,3-dicyanopropanoate
3) NH$_3$—H$_2$O, DCM

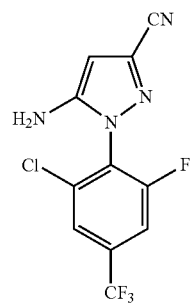

To a stirred concentrated H$_2$SO$_4$ (473 mL) was added NaNO$_2$ (81.63 g, 1.18 mol, 1.20 eq.) at 0~5° C. in several portions. Then the mixture was heated to 45~50° C. and stirred at this temperature for 1 hour. This acid mixture was cooled to 0° C. and reserved to use in the next step. To a solution of 2-chloro-6-fluoro-4-trifluoromethylaniline (210 g, 985.9 mmol) in acetic acid (1.05 L) was added concentrated H$_2$SO$_4$ (44.45 mL) at rt. Then the solution was added dropwise to the above H$_2$SO$_4$—NaNO$_2$ mixture at 0° C. Then the mixture was heated to 50° C. After stirring for 1 hour, this reaction mixture was added to a suspension of 1,2-dicyano-3-hydroxyprop-2-ene (224 g, 1.48 mol, 1.5 eq.) and anhydrous sodium acetate (1.68 kg, 20.4 mol, 13.78 eq.) in H$_2$O (1.05 L) at 5~10° C. After stirring for 1 hour, this reaction mixture was diluted with water and extracted with dichloromethane (DCM). The organic layers were stirred vigorously with 30% ammonium hydroxide solution overnight. The organic phase separated, dried over anhydrous Na$_2$SO$_4$, filtered and concentrated under vacuum to give yellow solid. The solid was recrystallized from ethyl acetate (EA) to afford 5-amino-1-(2-chloro-6-fluoro-4-(trifluoromethyl)-phenyl)-1H-pyrazole-3-carbonitrile as yellow solid (220 g, 73%).

$^1$H-NMR (300 MHz, CDCl$_3$) δ7.72 (s, 1H), 7.53 (dd, J=1.5 Hz, J=7.2 Hz, 1H), 6.08 (s, 1H), 3.83 (s, 2H)

MS: m/z=305 [M+H]$^+$

Step 4 Synthesis of 5-amino-1-(2-chloro-6-fluoro-4-(trifluoromethyl)phenyl)-4-(trifluoromethylsulfinyl)-1H-pyrazole-3-carbonitrile

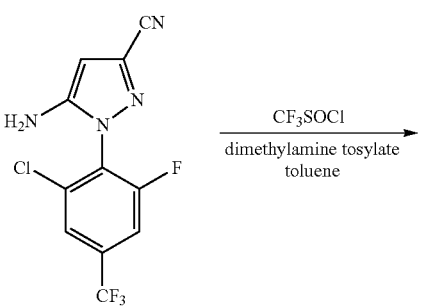

CF$_3$SOCl, dimethylamine tosylate, toluene

-continued

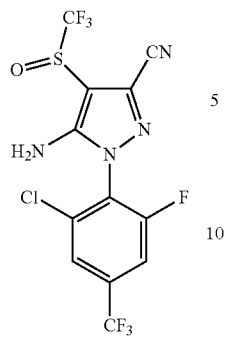

To a solution of 5-amino-1-(2-chloro-6-fluoro-4-(trifluoromethyl)phenyl)-1H-pyrazole-3-carbonitrile (140 g, 459.6 mmol, 1.00 eq.) and dimethylamine tosylate (151.8 g, 698.6 mmol, 1.52 eq.) in toluene (840 mL) was added CF₃SOCl (89.7 g, 588.3 mmol, 1.28 eq.). After the mixture was stirred at 40° C. for 16 h, nitrogen was bubbled through the solution and the solution was cooled to rt. Then the mixture was poured into 2 L ice/water and stirred at 0° C. for 1 h. The precipitated solid was isolated by filtration and dried under vacuum. The solid was recrystallized with toluene to give 5-amino-1-(2-chloro-6-fluoro-4-(trifluoromethyl)phenyl)-4-(trifluoromethylsulfinyl)-1H-pyrazole-3-carbonitrile (125 g, 64%) as yellow solid.

¹H-NMR (300 MHz, CDCl₃) δ7.77 (s, 1H), 7.61 (m, 1H), 5.26 (s, 2H)

¹⁹F NMR (282 MHz, CDCl₃) δ −63.40 (s, 3F), −74.71 (d, J=42.86 Hz, 3F), −110.96 (s, 1F)

MS: m/z=421 [M+H]⁺

Step 5 Synthesis of 5-bromo-1-(2-chloro-6-fluoro-4-(trifluoromethyl)phenyl)-4-(trifluoromethylsulfinyl)-1H-pyrazole-3-carbonitrile

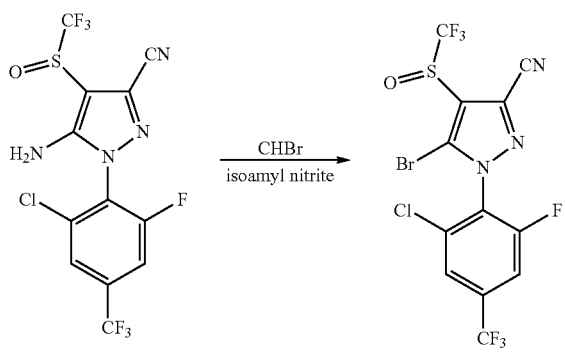 [SMILES: N#Cc1nn(-c2c(F)cc(C(F)(F)F)cc2Cl)c(N)c1S(=O)C(F)(F)F ; "CHBr" ; N#Cc1nn(-c2c(F)cc(C(F)(F)F)cc2Cl)c(Br)c1S(=O)C(F)(F)F]

To a solution of 5-amino-1-(2-chloro-6-fluoro-4-(trifluoromethyl)phenyl)-4-(trifluoromethylsulfinyl)-1H-pyrazole-3-carbonitrile (130 g, 310.3 mmol, 1.00 eq.) in CHBr₃ (520 mL) was added dropwise isoamyl nitrite (109 g, 930.8 mmol, 3.00 eq.) at 55~60° C. After all the isoamyl nitrite was added, the solution was stirred at 60° C. for 30 min. Then the mixture was concentrated under vacuum to give red solid. The solid was recrystallized with isopropyl alcohol to give 5-bromo-1-(2-chloro-6-fluoro-4-(trifluoromethyl)phenyl)-4-(trifluoromethylsulfinyl)-1H-pyrazole-3-carbonitrile (110 g, 73%) as yellow solid.

¹H-NMR (300 MHz, CDCl₃) δ7.78 (s, 1H), 7.61 (m, 1H).

MS: m/z=484 [M+H]⁺

Step 6: 1-(2-chloro-6-fluoro-4-(trifluoromethyl)phenyl)-5-methyl-4-(trifluoromethylsulfinyl)-1H-pyrazole-3-carbonitrile (Compound 1)

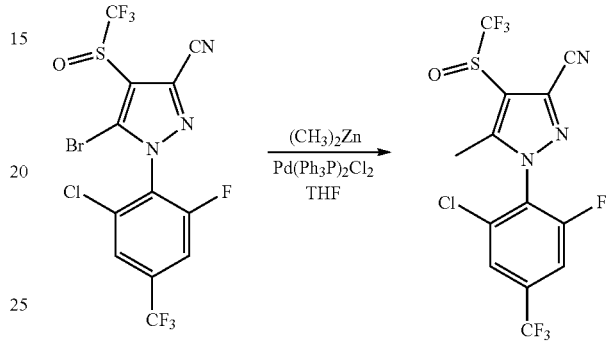

A solution of 5-bromo-1-(2-chloro-6-fluoro-4-(trifluoromethyl)phenyl)-4-(trifluoromethylsulfinyl)-1H-pyrazole-3-carbonitrile (210 g, 432 mol, 1.00 eq.) in degassed THF (600 mL) was added Pd(PPh₃)₂Cl₂ (15.18 g, 21.63 mmol, 0.05 eq.) under nitrogen. The reaction mixture was flushed with nitrogen. Then Me₂Zn (1.2 M in toluene) (300 mL, 360 mmol, 0.83 eq.) was added to the solution at rt. The resulted mixture was heated to 40~45° C. for 5 hours. Then the solution was cooled to rt and poured into ice/H₂O and extracted with ethyl acetate. The organic layers was dried, concentrated under vacuum and purified by silica gel (PE: EA=20:1~10:1) to give 115 g yellow solid. This solid was recrystallized with EtOH to afford 1-(2-chloro-6-fluoro-4-(trifluoromethyl)phenyl)-5-methyl-4-(trifluoromethylsulfinyl)-1H-pyrazole-3-carbonitrile (99 g, 54%) as white solid.

¹H NMR (300 MHz, CDCl₃) δ2.45 (s, 3 H), 7.59 (d, J=8.2 Hz, 1 H) and 7.76 (s, 1 H). ¹⁹F NMR (282 MHz, CDCl₃) δ −63.40 (d, J=29.61 Hz, 3F), −73.47 (dd, J=6.77 Hz, J=27.64 Hz, 3F), −112.60 (d, J=79.8 Hz, 1F)

MS: m/z=420 [M+H]⁺.

Example 3

Preparation of 1-(2,6-dicloro-4-trifluoromethyl-phenyl)-5-methyl-4-trifluoromethylsulfinyl-1H-pyrazole-3-carbonitrile (Compound 2) according to the second aspect of the invention Compound 2, was prepared using a process according to the second aspect of the invention as depicted in Scheme 3 and described below. The starting material for the process depicted in Scheme 3 is fipronil, a well-known and commercially available 5-aminopyrazole compound (see for example, EP 0 295 117). Compound 2 was prepared in only two steps from fipronil in an overall yield of 65%.

Scheme 3

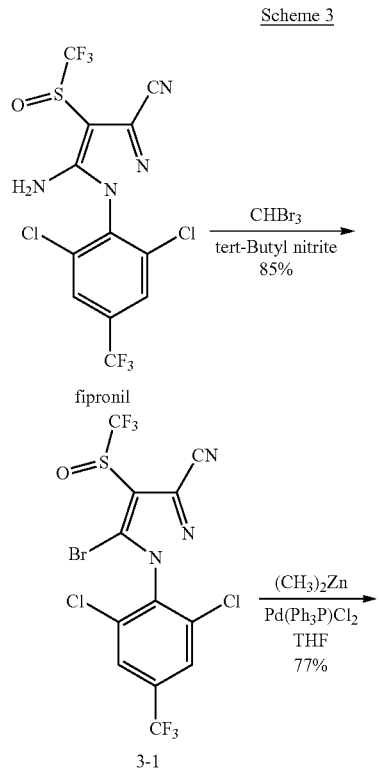

Step 1: 5-bromo-1-(2,6-dichloro-4-trifluoromethyl phenyl)-4-trifluoromethylsulfinyl-3-1H-pyrazole-3-carbonitrile (Compound 3-1)

1160 grams (20 eq.) of bromoform was charged to reaction vessel under an atmosphere of nitrogen followed by 100 grams of fipronil (1 eq.). The mixture was then heated to 50-60° C. and 1344 grams of tert-Butyl nitrite (2.0 eq.) was added. The mixture was aged for 3 hours at 55-60° C., at which time there was less than 1% starting material. After this time, the reaction mixture was concentrated under vacuum at 70-80° C. to one volume. The concentrated mixture was diluted with 5 volumes isopropyl alcohol and then heated to reflux at a rate of 10° C. per 10 minutes and aged for 30 minutes. The mixture was then cooled to about 0° C.±5° C. at a rate of 10° C. per 10 minutes and aged for half an hour at this temperature before filtering off the solid. The solid was washed with isopropyl alcohol and dried at about 40° C.±5° C. under vacuum to yield 92 g of the desired product as a yellow solid (80% yield, purity 98%).

Step 2: 1-(2,6-dicloro-4-trifluoromethyl-phenyl)-5-methyl-4-trifluoromethylsulfinyl-1H-pyrazole-3-carbonitrile (Compound 2)

600 milliliters (3.0 volumes) of tetrahydrofuran were charged to the reaction vessel under an atmosphere of nitrogen, followed by 200 g of Compound 3-1 (1.0 eq.). The mixture was degassed for 30 minutes by introduction of nitrogen to the solution. Then, 43 grams of Pd(Ph$_3$P)$_2$Cl$_2$ (0.018 eq.) was added to the vessel and the mixture was warmed to 25-30° C. This was followed by addition of 320 ml of a 1M solution of dimethylzinc in toluene dropwise at 25-35° C. The resulting mixture was heated to 35-45° C. and aged for 16 hours, at which time <1% of the starting material was present. After the reaction was confirmed to be complete, it was cooled to 20-25° C. and then added slowly to water (1.5 L). The mixture was extracted with ethyl acetate twice and the combined organic layers were washed with brine (two times). The organic layer was then stirred with activated carbon for 30 minutes at 20-25° C. and filtered. The filtrate was concentrated under vacuum at 40-45° C. to 1 volume and seven volumes of isopropyl alcohol were added. The diluted mixture was heated to reflux for one hour and then cooled to 10-15° C., aged for 5 hours and filtered. The solid is washed with isopropyl alcohol and dried at 35° C. under vacuum to produce 105 grams of a yellow solid (purity 98%, yield 60%).

Example 4

Preparation of 5-bromo-1-(2,6-dicloro-4-trifluoromethyl-phenyl)-4-trifluoromethylsulfinyl-1H-pyrazole-3-carbonitrile (Compound 3-1)

Compound 3-1, was prepared using another embodiment of the second aspect of the invention as described below.

Sixty grams of fipronil (137 mmoles, 1.0 eq.) was dissolved in 60 ml of acetonitrile at 20° C. in a reaction vessel with stirring. This was followed by addition over 30 minutes of 78 ml of a 48% solution of HBr in water (686 mmoles, 5 eq.). The resulting mixture was cooled to 0° C. and 28 grams of NaNO$_2$ (412 mmoles, 3.0 eq.) in 180 ml of water were added. After 30 minutes at 0° C., the reaction mixture was heated to 50° C. over 50 minutes and aged for an additional hour at 50° C., at which time the amount of fipronil was less than 1%. The mixture was concentrated to remove acetonitrile at 50° C., during which the product began to crystallize. The mixture was then cooled to 20° C. Isopropyl alcohol (10 ml, 0.2 volumes) was added and the mixture was stirred for 30 minutes at 20° C. The resulting mixture was filtered at 20° C. and the solid was washed with water (3×50 ml). The solid was dried at 50° C. under vacuum to afford 72.2 grams of the desired product. The crude product was purified by recrystallization from isopropyl alcohol (2.0 volumes) by heating the mixture to reflux followed by cooling to 20° C., filtering the product and washing the solid with isopropyl alcohol (2×0.5 volumes). The isolated solid was dried at 50° C. under vacuum to afford 37.66 grams of the product in 61.0% yield (97.4% purity).

Example 5

Preparation of 5-bromo-1-(2,6-dicloro-4-trifluoromethyl-phenyl)-4-trifluoromethylsulfinyl-1H-pyrazole-3-carbonitrile (Compound 3-1)

Compound 3-1, was prepared using another embodiment of the second aspect of the invention as described below.

Under a nitrogen atmosphere 102.2 grams of CuBr$_2$ (2.5 eq.) was added to 200 ml (2.5 volume) of acetonitrile. This was followed by addition of 28.31 g of tert-Butyl nitrite (1.5 eq.) and an additional 40 ml (0.5 vol.) of acetonitrile. The resulting mixture was heated to 60° C. and fipronil (80 g, 1 eq.) in 400 ml (5 vol.) was added with stirring over 30 minutes. The reaction mixture was then concentrated to 3 volumes by removal of acetonitrile by distillation (5 vol.) and the mixture was then cooled to 25° C. Methyl tert-Butyl ether (400 ml, 5 vol.), water (80 ml, 2 vol.) and 1 N HCl (140 ml, 3 vol.) were added and the mixture was agitated. The phases were allowed to settle and the acidic aqueous layer was removed. The organic layer was then sequentially washed with 20% ammonium hydroxide (400 ml, 5 vol.) and brine (400 ml, 5 vol.). The resulting organic layer was concentrated to 2 volumes by distillation. Distillation of the solvent was continued with the concomitant addition of 5 volumes (400 ml) of isopropyl alcohol to replace the acetonitrile. The mixture was heated to 80° C. and then cooled to 20° C. slowly to crystallize the product. The resulting mixture was filtered and the cake was washed with 0.5 volumes of isopropanol twice. The product was dried at 45° C. under vacuum to afford 72.15 g of the desired product (78.7% yield, 83% purity). The crude product was purified by recrystallization from two volumes isopropanol by heating to 80° C. then cooling slowly to 20° C. The isolated solid was dried at 45° C. under vacuum to yield 63.06 g (68.8% yield, purity 89.3%).

Example 6

1-(2,6-dicloro-4-trifluoromethyl-phenyl)-5-methyl-4-trifluoromethylsulfinyl-1H-pyrazole-3-carbonitrile (Compound 2)

Compound 2, was prepared from Compound 3-1 using another embodiment of the second aspect of the invention as described below.

Thirty seven grams of Compound 3-1 (0.07 mol, 1.0 eq.), 40.82 grams of potassium carbonate (0.30 mol, 4 eq.), 3.38 grams of $Pd_2(dba)_3$ (0.05 eq.) and 7.42 g of trimethylboroxine (0.06 mol, 0.8 eq.) were added to a reaction vessel containing 370 ml (10 vol.) of n-butyl acetate. The mixture was then heated to 120° C. over 1 hour and 40 minutes and aged for an additional 2.5 hours, at which time <1% of the starting material was present. The reaction mixture was then cooled to 20° C. The cooled reaction mixture was added to a separate vessel followed by a rinse of 50 ml (1.35 vol.) of n-Butyl acetate and stirred for 30 minutes at 20° C. with 1.85 grams of activated carbon. The resulting mixture was then filtered through diatomaceous earth (Celite® 545) and the cake washed with 50 ml n-Butyl acetate. Water (150 ml, 4 vol.) was added to the filtrate and the mixture stirred for 5 minutes at 20° C. The layers were allowed to separate and the aqueous layer was removed. The resulting organic layer was concentrated under vacuum to provide 31.2 grams of the product (97.0% yield, 76.6% purity). The crude product was purified by crystallization from isopropyl alcohol to provide desired product in 77.2% yield at a purity of 94.8%.

Example 7

1-(2,6-dicloro-4-trifluoromethyl-phenyl)-5-methyl-4-trifluoromethylsulfinyl-1H-pyrazole-3-carbonitrile (Compound 2)

Compound 2, was prepared from Compound 3-1 using another embodiment of the second aspect of the invention as described below.

The reaction of Compound 3-1 with 0.8 equivalents of trimethylboroxine using various polymer-supported catalysts was examined. The catalysts tested are sold by the trade name FibreCat® by Johnson-Matthey. The active palladium metal is covalently linked to a polymer chain and the active polymer is further linked to an inert polyolefin fiber that is insoluble in the reaction solvent. Thus, Compound 3-1 was mixed with 0.8 equivalents of trimethylboroxine, 4 equivalents of $K_2CO_3$ and 0.2 equivalents of the appropriate homogeneous polymer-supported palladium catalyst in n-butyl acetate and heated to 100° C.

The table below shows the results of the reaction using three different FibreCat® catalysts. The product may be isolated by simply filtering the reaction mixture and further processing the filtrate to remove the solvent or to crystallize the product from solution.

| Catalyst | Reaction time (h) (100° C.) | % Compound 3-1 (HPLC) | % Compound 2 (HPLC) | Estimated yield (HPLC assay) |
|---|---|---|---|---|
| FibreCat ® 1001 | 2 | 6 | 55 | 62 |
| FibreCat ® 1001 | 15 | Nd | 54 | 62 |
| FibreCat ® 1007 | 2 | 24 | 35 | 23 |
| FibreCat ® 1007 | 15 | 0.7 | 32 | 23 |
| FibreCat ® 1032 | 2 | 30 | 44 | 45 |
| FibreCat ® 1032 | 15 | Nd | 50 | 45 |

Nd = not detected

The example demonstrates that the second aspect of the invention may be conducted using a polymer-supported palladium catalyst.

Having thus described in detail various embodiments of the present invention, it is to be understood that the invention defined by the above paragraphs is not to be limited to particular details set forth in the above description as many apparent variations thereof are possible without departing from the spirit or scope of the present invention.

We claim:

1. A process for preparing a 1-aryl-5-alkyl pyrazole compound of formula (IB):

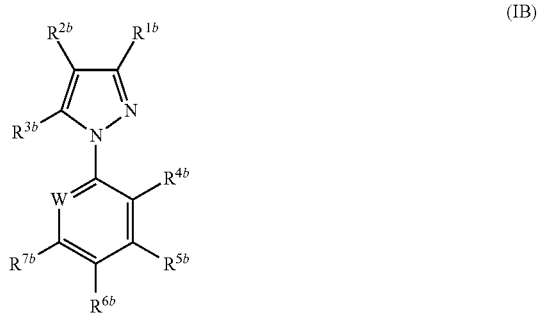

(IB)

wherein:
$R^{1b}$ is hydrogen, cyano, halogen, $R^{8b}$, formyl, —$CO_2H$, —$C(O)R^{8b}$, —$C(O)OR^{8b}$, —$C(O)NR^{9b}R^{10b}$ or —$C(S)NH_2$;
$R^{2b}$ is —$S(O)_mR^{11b}$;
$R^{3b}$ is alkyl, haloalkyl, hydroxyalkyl, cycloalkyl, halocycloalkyl, alkenyl, alkynyl, aryl, heterocyclyl, heteroaryl, $R^{8b}NH$, $(R^{8b})_2N$, $R^{8b}O$, $R^{8b}S$ or $R^{8b}C(O)CH_2$— wherein each alkyl, cycloalkyl, alkenyl, alkynyl, aryl, heterocyclyl or heteroaryl group may optionally be substituted by one or more of halogen, hydroxy, alkoxy, alkoxyalkoxy, amino, alkylamino, dialkylamino, nitro, cyano or —$C(S)NH_2$;
$R^{4b}$, $R^{5b}$, $R^{7b}$ and $R^{13b}$ are each independently hydrogen, halogen, alkyl, haloalkyl, cyano or nitro;
$R^{6b}$ is halogen, alkyl, haloalkyl, alkoxy, haloalkoxy, cyano, nitro, —$C(O)R^{12b}$, —$S(O)_nR^{12b}$ or $SF_5$;
W is nitrogen or C—$R^{13b}$;
$R^{8b}$ is alkyl, haloalkyl, hydroxyalkyl, cycloalkyl, halocycloalkyl, alkenyl, haloalkenyl, alkynyl, haloalkynyl, aryl, heterocyclyl or heteroaryl;

49

$R^{9b}$ and $R^{10b}$ are independently hydrogen, alkyl, haloalkyl, hydroxy or alkoxy;

$R^{11b}$ is alkyl, haloalkyl, alkenyl, haloalkenyl, alkynyl, haloalkynyl, cycloalkyl or halocycloalkyl;

$R^{12b}$ is alkyl or haloalkyl;

m is 0, 1 or 2; and n is 0, 1 or 2;

which comprises the steps:

step (i) reacting a compound of formula (IIB):

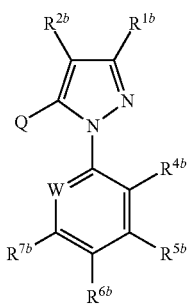

(IIB)

wherein $R^{1b}$ is hydrogen, cyano, halogen, $R^{8b}$, formyl, —CO$_2$H, —C(O)R$^{8b}$, —C(O)OR$^{8b}$, —C(O)NR$^{9b}$R$^{10b}$ or —C(S)NH$_2$;

$R^{2b}$ is —S(O)$_m$R$^{11b}$;

$R^{4b}$ is hydrogen, halogen, alkyl, haloalkyl, cyano or nitro;

$R^{5b}$ is hydrogen, halogen, alkyl, haloalkyl, cyano or nitro;

$R^{6b}$ is halogen, alkyl, haloalkyl, alkoxy, haloalkoxy, cyano, nitro, —C(O)R$^{12b}$, —S(O)$_n$R$^{12b}$ or SF$_5$;

$R^{7b}$ is hydrogen, halogen, alkyl, haloalkyl, cyano or nitro;

W is halogen, alkyl, haloalkyl, alkoxy, haloalkoxy, cyano, nitro, —C(O)R$^{12b}$, —S(O)$_n$R$^{12b}$ or SF$_5$; and Q is iodo, bromo, chloro or a haloalkylsulfonate group;

with a compound of formula (IIc):

R-M (IIc)

wherein

R is alkyl, haloalkyl, cycloalkyl, halocycloalkyl, alkenyl, alkynyl, aryl, heteroaryl or heterocyclyl, wherein each alkyl, cycloalkyl, alkenyl, alkynyl, aryl, heteroaryl or heterocyclyl group may optionally be substituted with one or more halogen, hydroxy, alkoxy, alkoxyalkoxy, amino, alkylamino, dialkylamino, nitro, cyano or —C(S)NH$_2$ groups;

M is MgX, ZnX, RZn, BY$_2$, BF$_3$ or SnR'$_3$;

X is iodo, bromo or chloro;

Y is OH or alkoxy, or each Y may be an alkoxy group which is part of a glycol derivative Y—(CR"R''')$_a$—Y where R" and R''' are independently hydrogen or C$_1$-C$_3$ alkyl and a is 2, 3 or 4; and R' is alkyl or haloalkyl;

or reacting the compound of formula (IIB) with R$^{8b}$NH$_2$, (R$^{8b}$)$_2$NH, R$^{8b}$OH, R$^{8b}$SH or an enolate anion R$^{8b}$C(O)CH$_2^-$, wherein R$^{8b}$ is as defined above for the compound of formula (IB);

in the presence of a transition metal catalyst to form the compound of formula (IB);

step (ii) wherein if R$^{1b}$ in the compound of formula (IB) is —C(O)OR$^{8b}$ or —C(O)NR$^{9b}$R$^{10b}$, optionally converting the —C(O)OR$^{8b}$ or —C(O)NR$^{9b}$R$^{10b}$ groups to cyano, hydroxyalkyl, aminoalkyl, dialkylaminoalkyl, formyl, —C(O)R$^{8b}$ or —C(S)NH$_2$, wherein R$^{8b}$, R$^{9b}$

50 and R$^{10b}$ are as defined above for the compound of formula (IB), via functional group modification; and step (iii) optionally oxidizing the group —S(O)$_m$R$^{11b}$ where m is 0 or 1, to form the compound of formula (IB);

wherein the sequence of steps ii) and iii) may be interchanged.

2. The process of claim 1, wherein the compound of formula (IIB) wherein Q is I, Br or Cl, is prepared by reacting a compound of formula (IIIB):

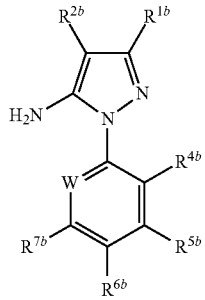

(IIIB)

wherein R$^{1b}$ is hydrogen, cyano, halogen, R$^{8b}$, formyl, —CO$_2$H, —C(O)R$^{8b}$, —C(O)OR$^{8b}$, —C(O)NR$^{9b}$R$^{10b}$ or —C(S)NH$_2$;

R$^{2b}$ is —S(O)$_m$R$^{11b}$;

R$^{4b}$ is hydrogen, halogen, alkyl, haloalkyl, cyano or nitro;

R$^{5b}$ is hydrogen, halogen, alkyl, haloalkyl, cyano or nitro;

R$^{6b}$ is halogen, alkyl, haloalkyl, alkoxy, haloalkoxy, cyano, nitro, —C(O)R$^{12b}$, —S(O)$_n$R$^{12b}$ or SF$_5$;

R$^{7b}$ is hydrogen, halogen, alkyl, haloalkyl, cyano or nitro; and

W is nitrogen or C—R$^{13b}$;

with a source of Br, Cl or I and a nitrite compound T-ONO;

wherein T is hydrogen or alkyl, or a salt thereof.

3. The process of claim 1, wherein the transition metal catalyst is a palladium catalyst.

4. The process of claim 2, wherein T-ONO is sodium nitrite, isopentyl nitrite, or tert-Butyl nitrite.

5. The process of claim 1, wherein Q is bromo.

6. The process of claim 1, wherein M is ZnX or RZn.

7. The process of claim 1, wherein M is BY$_2$.

8. The process of claim 7, wherein Y is hydroxy.

9. The process of claim 1, wherein R$^{3b}$ and R are methyl.

10. The process of claim 1, wherein in step (i) the compound of (IIB) is reacted with a compound of (IIc) wherein M is BY$_2$, and wherein the process further comprises addition of a base to the reaction mixture.

11. The process of claim 10, wherein the base is an alkali metal hydroxide or an alkali metal carbonate.

12. The process of claim 3, wherein the palladium catalyst is selected from (Ph$_3$P)$_4$Pd, (Ph$_3$P)$_2$PdCl$_2$, (CH$_3$CN)$_2$PdCl$_2$, Pd$_2$(dba)$_3$ or (dppf)PdCl$_2$.

13. The process of claim 2, wherein the compound of formula (IIIB) is fipronil.

14. The process of claim 4, wherein T-ONO is sodium nitrite and the source of Br is HBr.

15. A process for preparing a 1-aryl-5-alkyl pyrazole compound of formula (I):

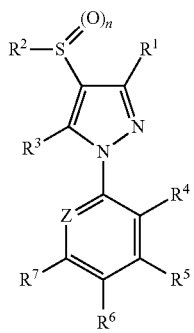

(I)

wherein:

- $R^1$ and $R^3$ are each independently hydrogen, cyano, hydroxyalkyl, alkoxyalkyl, aminoalkyl, alkylaminoalkyl, dialkylaminoalkyl, alkyl, haloalkyl, cycloalkyl, halocycloalkyl, alkenyl, alkynyl, formyl, aryl, heterocyclyl, heteroaryl, —C(O)R$^8$, —C(O)OR$^8$, —C(O)NR$^9$R$^{10}$ or —C(S)NH$_2$, wherein each alkyl, cycloalkyl, alkenyl, alkynyl, aryl, heterocyclyl or heteroaryl group may optionally be substituted by one or more of halogen, hydroxy, alkoxy, alkoxyalkoxy, amino, alkylamino, dialkylamino, alkyl or haloalkylthio; alkyl or haloalkyl sulfinyl; alkyl or haloalkyl sulfonyl; nitro, cyano and —C(S)NH$_2$;
- $R^2$ is alkyl, haloalkyl, alkenyl, haloalkenyl, alkynyl, haloalkynyl, cycloalkyl or halocycloalkyl;
- $R^4$, $R^5$, $R^7$ and $R^{12}$ are each independently hydrogen, halogen, alkyl, haloalkyl, cyano or nitro;
- $R^6$ is halogen, alkyl, haloalkyl, alkoxy, haloalkoxy, cyano, nitro, —C(O)R$^{11}$, —S(O)$_m$R$^{11}$ or SF$_5$;
- Z is nitrogen or C—R$^{12}$;
- $R^8$ is alkyl, haloalkyl, cycloalkyl or halocycloalkyl;
- $R^9$ and $R^{10}$ are independently hydrogen, alkyl, haloalkyl, hydroxy or alkoxy;
- $R^{11}$ is alkyl or haloalkyl;
- n is 0, 1 or 2; and
- m is 0, 1 or 2;

which comprises the following steps:

step (i) reacting a disulfide compound of formula (II) with an arylhydrazine of formula (III)

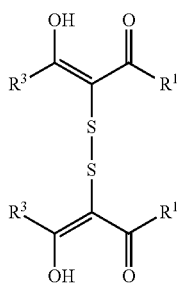

(II)

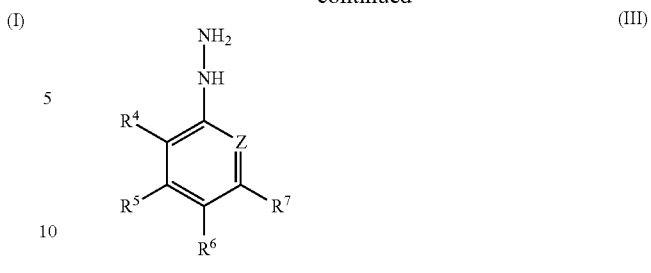

(III)

wherein $R^1$ and $R^3$ are each independently hydrogen, hydroxyalkyl, alkoxyalkyl, aminoalkyl, alkylaminoalkyl, dialkylaminoalkyl, alkyl, haloalkyl, cycloalkyl, halocycloalkyl, alkenyl, alkynyl, formyl, aryl, heteroaryl, —C(O)R$^8$, —C(O)OR$^8$, —C(O)NR$^9$R$^{10}$ or —C(S)NH$_2$, wherein each alkyl, cycloalkyl, alkenyl, alkynyl, aryl or heteroaryl group may optionally be substituted by one or more of halogen, hydroxy, alkoxy, alkoxyalkoxy, amino, alkylamino, dialkylamino, alkyl or haloalkylthio; alkyl or haloalkyl sulfinyl; alkyl or haloalkyl sulfonyl; nitro, cyano and —C(S)NH$_2$;

and $R^4$, $R^5$, $R^6$, $R^7$ and Z are as defined for the compound of formula (I), to form a pyrazole disulfide of formula (IV)

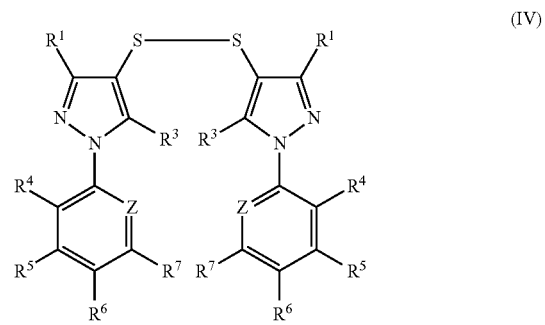

(IV)

wherein $R^1$, $R^3$ $R^4$, $R^5$, $R^6$, $R^7$ and Z are as defined for the compound of formula (I);

step (ii) reacting the compound of formula (IV) with a compound of formula (V)

$R^2$-LG     (V)

wherein $R^2$ is as defined above for the compound of formula (I) and LG is a leaving group to form a compound of formula (VI)

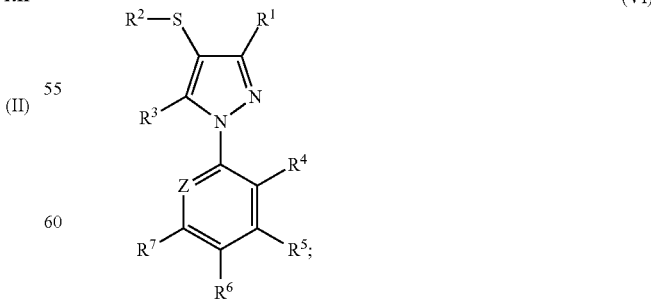

(VI)

step (iii) wherein if in the compound of formula (VI), $R^1$ or $R^3$ are —C(O)OR$^8$ or —C(O)NR$^9$R$^{10}$, optionally converting the —C(O)OR$^8$ or —C(O)NR$^9$R$^{10}$ groups in the compound of formula (VI) to cyano, hydroxyalkyl, aminoalkyl, dialkylaminoalkyl, formyl, —C(O)R$^8$ or —C(S)NH$_2$; and step (iv) optionally oxidizing the —SR$^2$ to form the compound of formula (I);

wherein the sequence of steps (iii) and (iv) may be interchanged.

16. The process of claim 15, wherein the disulfide of formula (II) is formed by reaction of the diketone of formula (VII)

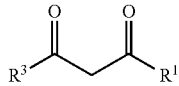

(VII)

with a disulfide dihalide reagent.

17. The process of claim 15, wherein in step ii) the reaction of the compound of formula (IV) with the compound of formula (V) is carried out in the presence of a reducing agent.

18. The process of claim 17, wherein the reducing agent is tetrakis(dimethylamino)ethylene, sodium borohydride, sodium dithionite, sodium hydroxymethanesulfinate, zinc hydroxymethanesulfoninate, formic acid or sodium formate.

19. The process of claim 15, wherein R$_2$ is alkyl or haloalkyl;

R$_1$ is —C(O)OR$^8$ or —C(O)NR$^9$R$^{10}$; and

R$^3$ is alkyl.

20. The process of claim 15, wherein in step (ii) the leaving group LG is iodide.

* * * * *